United States Patent
Bicalho

(10) Patent No.: US 10,500,253 B2
(45) Date of Patent: Dec. 10, 2019

(54) COMPOSITIONS AND METHODS USING IL-8 TO IMPROVE MILK PRODUCTION AND REPRODUCTIVE HEALTH IN MAMMALS

(71) Applicant: Cornell University, Ithaca, NY (US)

(72) Inventor: Rodrigo Carvalho Bicalho, Dryden, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/541,126

(22) PCT Filed: Jan. 5, 2016

(86) PCT No.: PCT/US2016/012154
§ 371 (c)(1),
(2) Date: Jun. 30, 2017

(87) PCT Pub. No.: WO2016/111992
PCT Pub. Date: Jul. 14, 2016

(65) Prior Publication Data
US 2018/0028615 A1 Feb. 1, 2018

Related U.S. Application Data

(60) Provisional application No. 62/099,643, filed on Jan. 5, 2015.

(51) Int. Cl.
| | |
|---|---|
| *A61K 38/20* | (2006.01) |
| *A61K 9/00* | (2006.01) |
| *A23K 20/147* | (2016.01) |
| *A23K 50/10* | (2016.01) |
| *A23C 9/20* | (2006.01) |
| *A61P 3/00* | (2006.01) |
| *A61P 15/14* | (2006.01) |

(52) U.S. Cl.
CPC ............ *A61K 38/2053* (2013.01); *A23C 9/20* (2013.01); *A23K 20/147* (2016.05); *A23K 50/10* (2016.05); *A61K 9/0034* (2013.01); *A61P 3/00* (2018.01); *A61P 15/14* (2018.01); *A23C 2230/10* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,108,875 A | 10/1963 | Bell | |
| 5,624,670 A * | 4/1997 | Kelly | A61K 38/2053 424/85.2 |
| 6,013,252 A | 1/2000 | Terao et al. | |
| 6,114,510 A | 9/2000 | Scholz et al. | |
| 2005/0232898 A1 | 10/2005 | Canning et al. | |
| 2006/0233748 A1 | 10/2006 | Merzouk et al. | |
| 2010/0112087 A1 | 5/2010 | Harrison et al. | |
| 2010/0113384 A1 | 5/2010 | Ametaj | |
| 2010/0298245 A1 | 11/2010 | Aydt et al. | |
| 2014/0206752 A1 | 7/2014 | Afeyan et al. | |

FOREIGN PATENT DOCUMENTS

| | | |
|---|---|---|
| EP | 0543476 A1 | 5/1993 |
| RU | 2405376 C2 | 12/2010 |
| WO | 2014/195413 A1 | 12/2014 |

OTHER PUBLICATIONS

Watanabe et al., Can. J. Vet. Res., 2008, vol. 72(3):291-296.*
Kimura et al., J. Dairy Sci., 2002, vol. 85(3):544-550.*
Lyubimov et al., Effect of mastitis on milk productivity activity of cows and fitness for processing, Vestnik Kazanskogo Gau, vol. 2, No. 28, pp. 130-134 2013.
Neves, et al., Use of leukocytes as treatment for endometritis in mares experimentally infected with *Streptococcus equi* subsp. *zooepidemicus*, Animal Reproduction Science, vol. 97, pp. 314-322 Feb. 20, 2006.
Zerbe, et al., Development and comparison of in vivo and in vitro models for endometritis in cows and mares, Theriogenology, vol. 60, pp. 209-223 2003.
Watanabe, A., et al., Effects of intramammary infusions of interleukin-8 on milk protein composition and induction of acute-phase protein in cows during mammary involution, The Canadian Journal of Veterinary Research, 2008, vol. 72, pp. 291-296.
Kimura, K., et al., Decreased Neutrophil Function as a Cause of Retained Placenta in Dairy Cattle, Journal of Dairy Science, 2002, vol. 85, pp. 544-550.
Barber et al., Chemotactic Activities in Nonmastitic and Mastitic Mammary Secretions: Presence of Interleukin-8 in Mastitic but Not Nonmastitic Secretions, Clinical and Diagnostic Laboratory Immunology, vol. 5, No. 1, pp. 82-86 Jan. 1998.
Muhaghegh-Dolatabady, Single Nucleotide Polymorphism in the Promoter Region of Bovine Interleukin 8 Gene and its Association with Milk Production Traits and Somatic Cell Score of Holstein Cattle in Iran, Iranian Journal of Biotechnology, vol. 12, No. 3, pp. 36-41 Nov. 25, 2014.
Galvao et al., Association between interleukin-8 receptor-alpha (CXCR1) polymorphism and disease incidence, production, reproduction, and survival in Holstein cows, Journal of Dairy Science, vol. 94, No. 4, pp. 2083-2091 Apr. 2011.

* cited by examiner

*Primary Examiner* — Xiaozhen Xie
(74) *Attorney, Agent, or Firm* — Hodgson Russ LLP

(57) ABSTRACT

The present disclosure provides compositions and methods for improving reproductive health of mammals and increasing milk production from female mammals. The methods involve administering an effective amount of IL-8 to a female mammal such that the reproductive health of the mammal is improved, or milk production from the mammal is increased, or the fat content of the milk is increased. In another aspect the disclosure includes prophylaxis and/or therapy of uterine conditions by administering IL-8 to a female mammal.

5 Claims, 13 Drawing Sheets

Specification includes a Sequence Listing.

Figure 15

Formatted alignments

```
                        10                    20                    30
Bos Taurus         M T S K L A V A L L A A F L L S A A L C E A A V L S R M S T
Bubalus bubalis    M T S K L A V A L L A A F L L S A A L C E A A V L S R M S T
Cervus elaphus     M T S K L A V A L L A A F L L S A A L C E A A V L S R M S T
Ovis aries         M T S K L A V A L L A A F L L S A A L C E A A V L S R M S T
Equus caballus     M T S K L A V A L L A V F L L S A A L C E A A V V S R I T A
Homo Sapen         M T S K L A V A L L A A F L I S A A L C E G A V L P R S A K
Canis lupus familiaris M T S K L A V A L L A A F V L S A A L C E A A V L S R V S S
Felis catus        M T S K L V V A L L A A F M L S A A L C E A A V L S R I S S
                   M T S K L A V A L L A A F L L S A A L C E A A V L S R   S
```
Predicted cleavage site by signal peptidase ↑

```
                        40                    50                    60
Bos Taurus         E L R C Q C I K T H S T P F H P K F I K E L R V I E S G P H
Bubalus bubalis    E L R C Q C I K T H S T P F H P K F I K E L R V I E S G P H
Cervus elaphus     E L R C Q C I K T H S T P F H P K F I K E L R V I E S G P H
Ovis aries         E L R C Q C I K T H S T P F H P K F I K E L R V I E S G P H
Equus caballus     E L R C Q C I K T H S K P F N P K L I K E M R V I E S G P H
Homo Sapen         E L R C Q C I K T Y S K P F H P K F I K E L R V I E S G P H
Canis lupus familiaris E L R C Q C I K T H S T P F H P K Y I K E L R V I D S G P H
Felis catus        E L R C Q C I K T H S T P F N P K L I K E L T V I D S G P H
                   E L R C Q C I K T H S T P F H P K F I K E L R V I E S G P H
```

```
                        70                    80                    90
Bos Taurus         C E N S E I I V K L T N G N E V C L N P K E K W V Q K V V Q
Bubalus bubalis    C E N S E I I V K L T N G K E V C L N P K E K W V Q K V V Q
Cervus elaphus     C E N S E I I V K L T N G K E V C L N P K E K W V Q K V V E
Ovis aries         C E N S E I I V K L T N G K E V C L D P K E K W V Q K V V Q
Equus caballus     C E N S E I I V K L V N G A E V C L N P H T K W V Q I I V Q
Homo Sapen         C A N T E I I V K L S D G R E L C L D P K E N W V Q R V V E
Canis lupus familiaris C E N S E I I V K L F N G N E V C L D P K E K W V Q K V V Q
Felis catus        C E N S E I I V K L V N G K E V C L D P K Q K W V Q K V V E
                   C E N S E I I V K L   N G   E V C L   P K E K W V Q K V V Q
```

```
                        100                   110                   120
Bos Taurus         V F V K R A E K Q D P - - - - - - - -
Bubalus bubalis    V F V K R A E K Q D P - - - - - - - -
Cervus elaphus     V F V K R A E K Q D P - - - - - - - -
Ovis aries         A F L K R A E K Q D P - - - - - - - -
Equus caballus     A F L K R T E - - - - - - - - - - - -
Homo Sapen         K F L K R A E N S L - - - - - - - - -
Canis lupus familiaris I F L K K A E K Q D P - - - - - - - -
Felis catus        I F L K K A E K Q N A - - - - - - - -
                   F L K R A E K Q D P
```

COMPOSITIONS AND METHODS USING IL-8 TO IMPROVE MILK PRODUCTION AND REPRODUCTIVE HEALTH IN MAMMALS

CROSS-REFERENCE TO RELATED APPLICATIONS

This application is a National Phase of International Application No. PCT/US16/12154, filed on Jan. 5, 2016, which claims priority to U.S. patent application No. 62/099,643, filed Jan. 5, 2015, the disclosures of each of which are incorporated herein by reference.

FIELD

This disclosure relates generally to improving milk production and reproductive health in mammals by administering Interleukin-8 (IL-8).

BACKGROUND

As the world population grows and more importantly as the per capita purchasing power parity increases, the demand for animal protein (milk, meat, and eggs) will steadily and inevitably grow; to avoid inflationary pressures the supply of animal protein products must increase significantly and sustainably with minimal expansion in agricultural land use. Additionally, it has been reported that feed efficiency is the single greatest factor contributing to variation in the carbon footprint, and that improving efficiency of feed conversion can reduce greenhouse gas emissions both via reductions in enteric methane and manure output. Post-partum uterine diseases such as metritis, endometritis, and retained placenta are important for animal welfare reasons, contributing to cow discomfort and elimination from the herd; coupled with profoundly affected reproductive performance, reduced milk yield and treatment costs. Metritis and endometritis are commonly associated with mixed bacterial infection of the uterus, including *E. coli, T. pyogenes*, and *F. necrophorum* (Bicalho et al., 2012). A contributory factor increasing susceptibility to uterine diseases is the immunosuppression faced by cows during the periparturient period (Drackley, 1999; Cai et al., 1994; Kimura et al., 1999; Hammon et al., 2006; Galvao et al., 2010). There is an ongoing and unmet need for improved approaches targeted to prophylaxis and therapy of post-partum diseases, as well as for improving reproductive performance and milk production. The present disclosure addresses these and other needs.

SUMMARY

In one aspect the present disclosure involves use of recombinant IL-8 to improve milk production by female mammals. IL-8 administration is also used for prophylaxis and/or therapy of one or more uterine diseases and for prophylaxis or therapy for hyperketonemia in female mammals.

In one embodiment the disclosure provides a method for improving health of a female mammal, and/or increasing milk production and/or fat content of milk produced by the mammal. The method comprises administering to the female mammal IL-8 such that at least the health of the female mammal is improved, and/or the mammal has increased milk and/or increased fat content in its milk.

In an embodiment, the IL-8 is administered to a pregnant female mammal, or to a female mammal subsequent to parturition, such as 12 months of parturition. In an embodiment, the IL-8 administration is accompanied by prophylaxis or treatment of metritis, or retained placenta, or an inhibition of hyperketonemia in the mammal, or a combination thereof. In embodiments, the IL-8 administration is oral, parenteral, subcutaneous, intramucosal or intraperitoneal. Parenteral administrations include intramuscular, intravenous, intraarterial, intraperitoneal, intravaginal, intrauterine, and subcutaneous administration. In an embodiment, the administration of the IL-8 is an intrauterine administration.

In various aspects, the disclosure provides for improving the health of the mammal by inhibiting development of puerperal metritis, or by inhibiting placenta retention, or by increasing milk production from the mammal, including but not limited to increasing energy corrected milk production, or by increasing fat content of the milk produced by the female mammal, or a combination of the foregoing.

In embodiments, the female mammal is a bovine mammal, such as a dairy cow. In embodiments, the female mammal is a member of a population of female mammals of the same species, and the IL-8 administration is given to other members of the population.

In another aspect the disclosure includes milk produced by a female mammal to which IL-8 has been administered, as well as dairy products produced using such milk.

In another aspect the disclosure includes a kit for i) improving health of a female mammal, and/or ii) increasing milk production and/or fat content of milk produced by the mammal, the kit comprising IL-8 in one or more sealed containers, a delivery device, and instructions for introducing IL-8 to a female mammal to obtain i) or ii). The delivery device can be suitable for introducing the IL-8 into the uterus of a non-human mammal.

In another aspect the disclosure includes an article of manufacture comprising IL-8 in a sealed container, packaging, and printed information, the printed information identifying IL-8 as a content of the package and providing an indication that the IL-8 is to be used for improving health of a female mammal, and/or ii) increasing milk production and/or fat content of milk produced by the mammal.

DESCRIPTION OF THE FIGURES

FIG. 15: Representative amino acid sequence alignments of IL-8 from select animal species. The sequences are shown from N- to C-termini. The sequence for each species and the consensus sequence is contiguous throughout the rows. The *Bos taurus* sequence is SEQ ID NO:1. The *Bubalus bubalus* sequence is SEQ ID NO:4. The *Cervus elephus* sequence is SEQ ID NO:5. The *Ovis aries* sequence is SEQ ID NO:6. The *Equus caballus* is SEQ ID NO:7. The *Homo sapiens* sequence is SEQ ID NO:8. The *Canis lupus familiaris* sequence is SEQ ID NO:9. The *Felus catus* sequence is SEQ ID NO:10. The consensus of the specific mammal sequences shown in the bottom row is SEQ ID NO:11.

DETAILED DESCRIPTION

Figure 1:
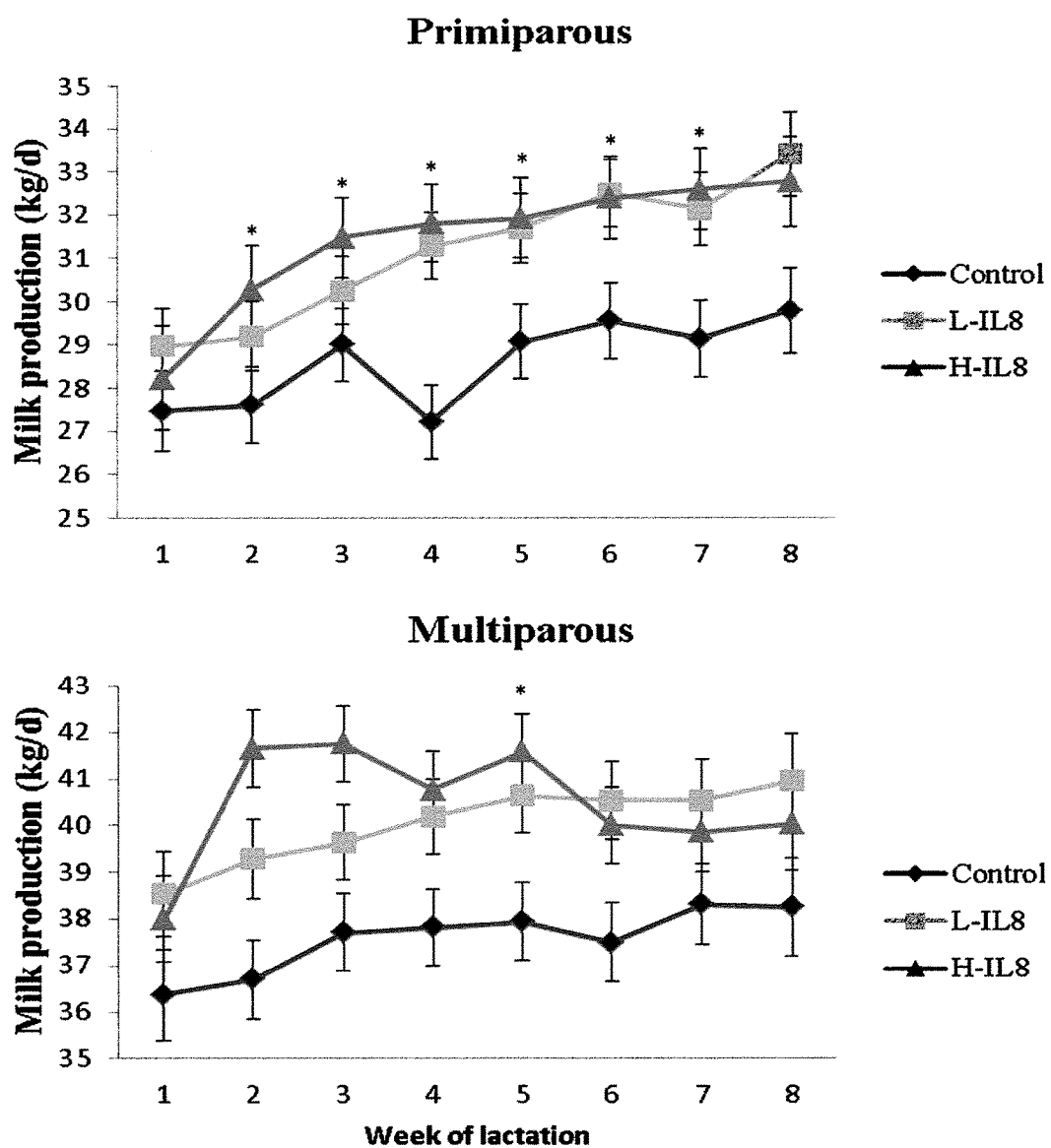
FIG. 1: Milk production (kg/d) by week of lactation for primiparous and multiparous cows. The error bars stand for the standard error of the mean. The overall milk production was higher for L-IL8 and H-IL8 cows compared to control cows (P-value<0.01). The interaction between treatment and week of lactation was not significant (P-value=0.06). An asterisk (*) indicates weekly means differ (P-value<0.05).

The present disclosure relates generally to administering an effective amount of IL-8 to female mammals with the intent of improving the health of the female mammals, which can comprise prophylaxis and/or therapy of one or more uterine diseases and/or hyperketonemia, and increasing milk production and/or fat content of milk, and combinations thereof. The disclosure thus encompasses administering an effective amount of IL-8 to a mammal such that milk production by the mammal is increased, and/or the fat content of milk produced by the mammal is increased, and/or the mammal has reduced uterine disease and/or reduced hyperketonemia. In embodiments the milk produced by the mammal is increased and collected. In embodiments reduced uterine disease includes but is not necessarily limited to reduced endometritis and/or puerperal metritis, and/or reduced retained placenta.

With respect to uterine diseases, as is known in the art, metritis generally involves inflammation of the wall of the uterus, while endometritis generally involves inflammation of the endometrium. In this regard, the present discovery that exogenously administered IL-8 has beneficial effects on uterine health was unforeseen because, among the known functions of IL-8 is its association with inflammation. Further, the serendipitous discovery of the favorable effects of IL-8 on milk fat content and milk production as further described below was unexpected. In view of these findings, the methods of the present disclosure result in an increase in the health of a female mammal as evidenced by, for example, increasing milk production, increasing fat corrected milk production, increasing energy corrected milk production, reducing the incidence of retained placenta, reducing the incidence or severity of metritis, or clinical endometritis, or puerperal metritis, or by improving the body condition score of the mammal at parturition, or reducing ketosis, including but not necessarily limited to reducing hyperketonemia, or reducing rectal temperature, or combinations thereof. Thus, the disclosure includes a variety of ways by which the general health and reproductive function of female mammals can be improved.

Those skilled in the art will recognize that energy corrected milk (ECM) is the amount of energy in milk based upon milk, fat and protein and adjusted to 3.5% fat and 3.2% protein. The conventional ECM formula is ECM=(0.327× milk lbs.)+(12.95×fat lbs.)+(7.65×protein lbs.).

It is expected that methods of the present disclosure will be applicable to any female mammal. In embodiments, the disclosure is directed to veterinary approaches, and thus in this aspect pertains to non-human mammals. In embodiments, the non-human female mammal to which IL-8 is administered is a ruminant, including but not necessarily limited to bovines, sheep, antelopes, deer, giraffes, and their relatives, and further can include pseudoruminants, such as the camelids. In embodiments, the ruminant is a female bovine mammal that is a member of the genus *Bos*, such as oxen, cows, and buffalo. In one embodiment the ruminant is a dairy cow. In embodiments the dairy cow is a primiparous or multiparous cow. In embodiments, the female mammal is an ungulate.

In an embodiment the disclosure includes administering IL-8 to a member of the genus *Sus*, and therefore encompasses practicing the invention with any swine, examples of which are not limited to the domestic pig (i.e., *Sus domesticus*), also commonly referred to as a swine or a hog.

The disclosure also includes administering IL-8 to non-bovine and non-ruminant mammals, including but not necessarily limited to equines, canines, and felines. In embodiments the disclosure includes administering IL-8 to aquatic mammals, such as cetacean mammals, examples of which are not necessarily limited to whales, dolphins and porpoises. Thus, the invention in certain aspects pertains to companion animals, as well as animals kept in conservation settings, for example in zoos or aquariums.

The methods described herein are also expected to be suitable for use with humans, such as by administering IL-8 to a human female for the purpose of increasing milk production or increasing the nutritional value of milk by increasing its fat content.

Particular implementations of this disclosure may also exclude IL-8 administration under certain circumstances. For example, in certain approaches, IL-8 administration is not given to a mammal from which milk is not obtained subsequent to the IL-8 administration. In certain embodiments, milk obtained subsequent to IL-8 administration to, for example, a dairy cow, is suitable for human consumption. Thus, in certain embodiments the IL-8 administration is to a non-human mammal from which milk is intended to be obtained and/or is obtained, wherein the milk is for human consumption and/or is consumed by humans. In certain aspects the disclosure may exclude IL-8 administration to particular types of mammals. In one example, the IL-8 is not given to a rodent. The disclosure can thus comprise administering IL-8 to all types of mammals, except rodents, specific examples of which include but are not limited to mice, rats and guinea pigs. In another example primates, including either or both human and non-human primates, can be excluded from the group of mammals to which the IL-8 is given. In one example the mammal to which IL-8 is administered does not have thrombosis, including but not limited to deep vein thrombosis. In certain embodiments the disclosure may exclude IL-8 administration during certain time periods, for example, in certain embodiments the disclosure may exclude IL-8 administration during pregnancy for the purpose promoting fertilization, implantation, or to induce uterine contractions. In certain aspects, IL-8 is not administered to a species of mammal for which acute inflammation after coitus is beneficial to and/or promotes conception. In certain embodiments the IL-8 is not administered by direct infusion into mammary tissue or a teat, and thus in embodiments the IL-8 administration does not induce or promote mastitis.

IL-8 is well known in the art as a chemokine produced by a number of different cell types, including macrophages. It is also referred to as CXCL8, and binds with specificity to the CXCR1 and CXCR2 receptors. It is produced as a precursor protein which is typically between 99 amino acids (for human IL-8), and up to 103 amino acids for other species, and undergoes cleavage to produce active isoforms. The cleaved version of human IL-8 that is most frequently secreted by human macrophages is 72 amino acids in length. In connection with this, while certain representative examples of the effects of recombinant bovine IL-8 administration to dairy cows are provided in this disclosure, it is expected that any IL-8 expressed by any animal can be used in the methods of the invention. In non-limiting embodiments, the IL-8 is a recombinantly produced *Bos taurus* IL-8 which comprises the following sequence or a fragment of:

```
                                        (SEQ ID NO: 1)
MTSKLAVALL AAFLLSAALC EAAVLSRMST ELRCQCIKTH
STPFHPKFIK ELRVIESGPH CENSEIIVKL TNGNEVCLNP
KEKWVQKVVQ VFVKRAEKQD P
```

In embodiments, the IL-8 is the processed form, and thus is shorter than a precursor IL-8 sequence. In embodiments, the IL-8 is at least 70 amino acids in length. In embodiments, the IL-8 used in the methods of this disclosure have at least 70 contiguous IL-8 amino acids, wherein the at least 70 amino acids have at least 70.0% homology to the bovine sequence presented above, and/or to the consensus sequence presented in FIG. 15 (bottom row of alignment). In embodiments, the IL-8 comprises or consists of a sequence having that is between 70-100% identical to the *Bos Taurus* sequence across 70, 71, 72, 73, 74, 75, 76, 77, 78, 79, or 80, or more, contiguous amino acids thereof. In embodiments, such sequence identity and length is relative to the amino acid sequence beginning at the N-terminus, or beginning at any amino acid from the N-terminus through amino acid position 2-25, inclusive, and including each amino acid position there between. In embodiments, the IL-8 comprises or consists of the sequence or a fragment of any amino acid sequence presented in FIG. 15. In an embodiment, the IL-8 comprises a change of the ELR to AAR in the *Bos Taura* sequence shown in FIG. 15 (SEQ ID NO:1).

IL-8 used in methods of this disclosure can be obtained from any suitable source. In one embodiment, the IL-8 is obtained commercially from a vendor. For example, human IL8 expressed in *E. coli* and provided as a lyophilized powder can be obtained from Sigma Aldrich. Bovine IL-8 can be obtained from Kingfisher Biotech, Inc., of Saint Paul, Minn. Alternatively, the IL-8 can be produced recombinantly using techniques well known to those skilled in the art, such as by using a protein expression system.

In a non-limiting and illustrative embodiment, IL-8 is produced recombinantly using the following approach, or modifications thereof that will be apparent to those skilled in the art given the benefit of the present disclosure. Plasmid construction. A pET28-His-L-EK-IL8 was constructed by subcloning from Trc-His-L-EK-IL8 into pET28A (NOVAGEN, Darmstadt, Germany) using the restriction sites NheI and XhoI. The original Trc plasmid was constructed by PCR amplification of the codon optimized bovine IL-8 cDNA ΔSS using the following nucleotides; 5'-C GGCGCC GTG CTG TCT CGT ATG TCC ACC GAA C (SEQ ID NO:2) and 5'-G CTCGAG TCA CGG ATC TTG TTT TTC TGC ACG (SEQ ID NO:3). The PCR product was TA cloned into a pGEM T vector (PROMEGA, Madison, Wis.) and was sequenced following blue white screening. The correct clone was then digested with the restriction enzymes SfoI and XhoI and ligated into a pTrcHis B vector (Invitrogen, Carlsbad, Calif.). To maintain a native version of IL-8 upon enterokinase cleavage, the Trc vector was prepared by digestion with BamHI followed by digestion with mung bean nuclease to remove the 5' overhang and create a blunt end for ligation, the vector was then digested with XhoI. The final construct was confirmed by sequencing.

Expression of the recombinant IL-8. To determine the *E. coli* BL21 preferred expression conditions for IL-8 full version and truncated form (without signal peptide), coding sequences were cloned in pET vector, a time course pilot was performed as follows. All growth steps were incubated at 37° C., at 200 rpm in LB broth or plates, containing 300 µg/ml of Kanamycin, in the 125 Erlenmeyer or Petri Dishes. Frozen stock cultures (−80° C.) were reactivated overnight on 20 ml of medium. The next day, 0.4 ml of the growth culture was transferred to 40 ml of fresh media and 1 mM of IPTG was added when the O.D. reached 600 nm, 1 ml aliquot was removed prior to IPTG induction and at one hour intervals over 4 hours. Each sample was centrifuged at 10,000 g for 5 min and the pellets were resuspended in lysing buffer (10 mM of Tris-HCL; 1 mM of EDTA; 0.1 N of NaOH; 0.5% SDS). Subsequently the insoluble proteins and cell debris were pelleted for 10 minutes at 13,000 g at 4° C. The supernatant was boiled with Laemmli buffer (63 mM of Tris-HCL ph 6.8; 10% glycerol; 2% SDS-electrophoresis-grade, 0.1% β-mercaptoethanol, and 0.0005% Bromphenol blue) for 5 minutes to load a 12% SDS-polyacrylamide gel. The electrophoresis was performed at 80 V during 90 minutes. The gel was stained with stain solution for 30 minutes and destained with destaining solution (Bio-Rad) for 2 hours under vigorous shaking. We expressed (pET28-His-LEK-IL8) IL8 in *E. coli*. The expressed pET28-His-LEK-IL8 is partially soluble and convenient for purification.

Compositions comprising IL-8 for use in the methods of this disclosure can be provided in a variety of forms and delivered via a variety of routes. Compositions for use in humans or non-human mammals can be prepared by mixing IL-8 with any suitable pharmaceutically acceptable carriers, excipients and/or stabilizers. Some examples of compositions suitable for mixing with IL-8 can be found in: Remington: The Science and Practice of Pharmacy (2005) 21st Edition, Philadelphia, Pa. Lippincott Williams & Wilkins. In certain aspects, IL-8 can be added to the feed of a mammal, and thus consumed as a dietary additive to support reproductive health and/or milk production.

Compositions comprising IL-8 can be administered to the mammal using any available method and route, including oral, parenteral, subcutaneous, intraperitoneal, intrapulmonary, and intranasal administrations. Parenteral infusions include intramuscular, intravenous, intra-arterial, intraperitoneal, intravaginal, intrauterine, and subcutaneous administration. The composition can be administered via an intramucosal approach. The administration of IL-8 can be performed before or after birth, and can be performed during pregnancy.

In certain embodiments, subject to certain provisos as further described herein, compositions comprising IL-8 are administered to a pregnant mammal, and thus a prepartum administration is used. In certain approaches the prepartum administration is performed during the mammogenesis period which varies from species to species but is within the last third of the gestation. As a non-limiting illustration, in an embodiment, the gestation period of a Holstein cow is 280 days. Thus, the administration of IL-8 after approximately 180 days of gestation is believed, without intending to be bound by theory, to help the development of the mammary gland leading to an increase in milk production in the postpartum period.

In an embodiment, a prepartum administration comprises an intravaginal administration of an IL-8 containing composition. In one non-limiting example, an intravaginal administration of an IL-8 containing composition is administered to a pregnant mammal, such as a dairy cow.

In certain embodiments, compositions comprising IL-8 are administered to a mammal that has recently given birth, and thus a postpartum administration is used. In embodiments, a postpartum intrauterine administration is used. In one non-limiting example, a postpartum intrauterine administration of an IL-8 containing composition is administered to a mammal, such as a dairy cow, within 72 hours of giving birth (parturition). Administering within shorter or longer times after parturition is also encompassed by this disclosure. In certain non-limiting examples, the composition comprising IL-8 is administered immediately post partition, and up to 20 weeks after parturition. In certain approaches the disclosure thus includes administering on the same day as parturition, or within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140 days, inclusive, and including all ranges of integers there between.

In certain approaches, the disclosure comprises, as an alternative to exogenous IL-8 administration, stimulating endogenous IL-8 production such that one or more of the effects described herein are produced. In non-limiting examples, stimulating exogenous IL-8 production comprises administering to a mammal one or more IL-8 stimulating compounds and/or compositions, including but not necessarily limited to tumor necrosis factor alpha (TNF-α), lipopolysaccharide (LPS), an interleukin-1 (IL-1), platelet-activating factor (PAF), and/or other substances that will can be used in embodiments of the instant invention, given the benefit of the present disclosure.

In certain embodiments the present disclosure comprises administration of an IL-8 containing composition to one or more mammals, a non-limiting example of which is a dairy cow(s), such that any one or any combination of the following is achieved: i) an increase in milk production; ii) an increase in energy corrected milk production; iii) an increase in fat content of milk produced by the mammal; iv) a reduction in the development of puerperal metritis, and/or a reduction in the incidence of puerperal metritis when the IL-8 administration is given to a plurality of mammals; v) a reduction in development of clinical endometritis, and/or a reduction in the incidence of clinical endometritis when the IL-8 administration is given to a plurality of mammals; vi) a reduction in hyperketonemia, such as a reduction in subclinical ketosis, and/or the incidence of subclinical ketosis when the IL-8 administration is given to a plurality of mammals, and vii) inhibiting retained placenta. In embodiments, the foregoing effects of IL-8 administration are achieved by using an intrauterine administration of the IL-8 containing composition, but it is considered that other administration routes could also be used.

It will be recognized that any of the foregoing results produced as a result of IL-8 administration can be compared to a reference to assess the effect of the IL-8 administration. Any suitable reference can be used, and those skilled in the art will recognize suitable references given the benefit of this disclosure. In embodiments, the reference can be a single value or a range of values. For example, a reference can be a standardized curve or an area on a graph. The reference can comprise a positive or negative control. In embodiments the reference comprises a measurement made from a sample obtained from a mammal to which IL-8 was not administered, or a different amount of IL-8 was administered, or a different IL-8 dosing schedule was used. In various aspects a measurement of a result can be compared to a reference to provide a qualitative or quantitative determination of the result, which may be positively or negatively correlated with IL-8 administration. In certain embodiments, comparison to a reference can be performed by an individual skilled in animal handling or testing. For example, retained placenta and metritis can be diagnosed by trained farm personnel according to specific protocols known in the art, and certain measurements as compared to a non-retained placenta or non-metritis condition can be made by those individuals, whether or not a direct comparison to a suitable reference is made. For example, in certain embodiments, a change in uterine discharge, such as the appearance of fetid, watery, red brown uterine discharge accompanied with fever can be used to diagnose puerperal metritis, whereas post-parturition cows which do not produce uterine discharge with such characteristics are determined to not have puerperal metritis.

This disclosure includes administering IL-8 to any one, or more than one mammal, such as a plurality or population of mammals. In an embodiment, the plurality of mammals comprises a group of dairy cows which can be present in, for example, a dairy farm of any scale, ranging from a few dairy cows to a commercial dairy farm which may house thousands of dairy cows.

As will be recognized from the results presented in the Examples and Figures of this disclosure, representative but non-limiting experiments demonstrate the foregoing enumerated effects using intrauterine and intravaginal infusions comprising a range if IL-8 amounts. In particular and non-limiting examples, aspects of the disclosure are demonstrated using 9.5 mg, 1.125 mg, 0.095 mg, 0.0095 mg, and 11.25 µg of recombinant IL-8. Thus, the disclosure demonstrates that a wide range of IL-8 amounts can elicit some or all of these effects, and given the benefit of this disclosure those skilled in the art will recognize how to modify IL-8 dosing to obtain a desired result in any particular mammal. Further, the disclosure includes a demonstration that IL-8 doses ranging from 9.5 mg, to as little as 0.0095 mg, produce a statistically significant increase in milk fat percentage. Accordingly, the disclosure includes administering an effective amount of IL-8, wherein the effective amount of IL-8 is an amount that results in a desired outcome. In one embodiment, the amount of IL-8 is from 0.001 µg to 10 mg, including all integers and amounts there between to the 0.001 unit, and all ranges of µg and mgs there between. In embodiments, at least 11.25 µg of IL-8 is administered to the mammal. In connection with this, the form and character of the particular IL-8 dosing regimen will be dictated by the route of administration and other known variables, taking into account such factors as the size, health, age, type of mammalian species, numbers of previous births (if any), previous history of uterine or other related conditions, and risk factors related to uterine conditions and milk production. In an embodiment, the mammal is in need of an IL-8 administration because of, for example, having a risk for or otherwise being predisposed to a uterine condition, or because of poor milk production. In embodiments, the administration of IL-8 is prophylactic or therapeutic, or both.

IL-8 compositions of this disclosure can be administered once or in a series of dosages, and can be administered concurrently or sequentially with any other compound or composition intended to improve the general health of the mammal, or for the specific purpose of promoting or enhancing the IL-8-induced effects described herein. In embodiments, the IL-8 administration is used in conjunction with an antibiotic, a hormone, or a growth factor. In certain approaches, IL-8 is administered only a single time, yet produces a durable effect on any one or combination of health and/or milk production outcomes as described herein.

Administration of an IL-8 composition can result in increased milk production, and/or milk with an increased fat content, for various periods of time subsequent to the administration. Desired milk fat content can be determined using any suitable method, several of which are known in the art. For example, milk fat content can be determined by the so-called Babcock test or Gerber Method. In embodiments, the fat content of milk is increased. The present disclosure provides a demonstration of an increase in milk fat in milk obtained from dairy cows subsequent to intrauterine and intravaginal infusions of recombinant IL-8. Thus, in certain approaches, the disclosure includes methods for stimulating production of milk with increased fat, and includes the milk produced by such methods.

In certain aspects, the disclosure includes elevating milk fat in milk produced by a dairy cow relative to a control, such as an amount of milk fat in milk produced by a dairy cow that did not receive an IL-8 administration. In certain approaches, the increased milk fat comprises an increase of milk fat (relative to a control) of at least 0.01% to 0.5%, inclusive, and including all numbers to the second decimal point there between, and all ranges of such numbers. In certain approaches, milk produced according to an embodiment of this disclosure comprises at least 3.4% milk fat, and may comprise from 3.4%-4.4% milk fat, including all numbers to the second decimal point there between, and all ranges of such numbers. In certain approaches milk comprises such amounts of milk fat when first obtained from the mammal. Thus, the stated amounts may be present in unprocessed milk.

Practicing methods of this disclosure has in certain embodiments one or more effects on the mammal that is durable for a period of time. For example, we have demonstrated increased the production of milk and fat corrected and energy corrected milk for 11 months from a single IL-8 administration. In certain implementations, the administration of IL-8 results in increased milk production, or increased fat corrected and/or energy corrected milk production, and/or an increase in fat content of milk, for a period of at least 1, 2, 3, 4, 5, 6, 7, 8, 9, 10, or 11 months subsequent to the IL-8 administration. Longer time periods are also encompassed. In certain approaches, IL-8 administration produces a durable effect on milk production that extends throughout a single lactation period, i.e., the entire period of lactation immediately subsequent to or during which the IL-8 is administered. In one example, the lactation period ends with a subsequent pregnancy. The disclosure includes in one non-limiting approach administering IL-8 in a single dose such that one or more effects on milk content and/or production as described herein persist for a period of at least 1, 2, 3, 4, 5, 6, 7, 8, 9, 10, or 11 months, or an entire period of lactation subsequent to or during which the single IL-8 administration is performed. In certain embodiments, one or more effects of IL-8 begin within a period of 1, 2, 3, 4, 5, 6, or 7 days of IL-8 administration and can persist thereafter according to any of the time periods described herein.

In certain aspects, the disclosure comprises increasing the amount of milk produced by a mammal, such as a dairy cow. In certain aspects, the increase in milk production comprises an increase of at least 1, 2, 3, 4, 5, 6, 7, 8, 9, 10, 11, or 12 pounds of milk per day. The increase in milk production can be assessed relative to a control, such as a dairy cow to which IL-8 is not administered. Those skilled in the art will recognize that a value of any IL-8 induced change described herein can be taken as, for example, an average value determined from a group of mammals over a period of time.

In another embodiment, the disclosure includes obtaining milk, and includes the milk itself, from a mammal treated with IL-8 as described above. This aspect comprises administering IL-8 to a female mammal and collecting milk produced subsequent to the administration. In one embodiment the milk produced by this process differs from other types of milk in that it has an increased fat content, such as milk fat content as described above. In embodiments, containers containing milk obtained from a mammal treated with IL-8 are provided. The containers can be any container, such as a consumer oriented container, for example a milk carton, or larger containers, such as a vat, or containers suitable for shipping or otherwise transporting large quantities of milk. In embodiments products made using milk obtained from a process describe herein are provided. Non-limiting examples of such products include cheese, yogurt, milk-based creams and creamers, ice cream, dairy based toppings, and any other dairy product made with said milk. Thus, in embodiments the dairy product can comprise a derivative of the milk, such as one or more separated components of the milk, including but not limited to the milk fat. Accordingly the milk can be processed to separate milk components for including in a variety of dairy products. The disclosure includes making such products using conventional approaches, but by substituting milk of this disclosure for previously available milk.

In another aspect the present invention provides articles of manufacture, such as a kit. The kit can include a pharmaceutical composition comprising IL-8 in one or more sealed containers, i.e., glass or plastic vials. The kit can include a syringe, a catheter or other delivery device. For example, in the case of a catheter it may be an artificial insemination (A.I.) catheter, such as a Gilt A.I. catheter, or equivalents. The kit can also include a bag, such as a bag that is suitable for containing a solution and adapted for use with the catheter for introducing a solution into a mammal, for instance by intravaginal or intrauterine delivery. The kit may optionally include instructions for use of its contents either written on a paper or in a computer-readable format. The kit can also contain IL-8 that is to be mixed with a carrier, such as IL-8 in a lyophilized form, and in this case the kit can further include instructions for reconstituting the lyophilized IL-8 into a carrier/solution for administration to the mammal. For example, the carrier may be sterile water, normal saline, or phosphate buffered saline. The carrier may be provided in one or more separate vials.

In another aspect the instant disclosure comprises an article of manufacture. The article of manufacture comprises IL-8 provided in packaging. The packaging can comprise a container, or can itself be a container. Any suitable container can be used, such as a plastic or glass container, including but not limited to plastic or glass vials. In various embodiments, the article of manufacture includes printed material. The printed material can be part of the packaging, or it can be provided on a label, or as paper insert or other written material included with the packaging. The printed material provides information identifying IL-8 as contents of the package, and instructs a consumer how to use the IL-8 to produce any one or any combination of the effects on mammals as described herein.

In view of the foregoing, and without intending to be bound by any particular theory, the present invention relates in part to the observation that a contributory factor that increases susceptibility to uterine diseases is the immunosuppression faced by cows during the periparturient period (Drackley, 1999; Cai et al., 1994; Kimura et al., 1999; Hammon et al., 2006; Galvao et al., 2010). Neutrophils are the main leukocyte type involved in placental release (Kimura et al., 2002), and in bacterial clearance after uterine (Hussain, 1989) and mammary gland (Paape et al., 2002) infection. Blood neutrophil function begins to decline prior to parturition, reaches a nadir shortly after parturition, and slowly returns to prepartum levels by about 4 weeks postpartum (Kehrli and Goff, 1989; Goff and Horst, 1997). Several factors can account for the loss in neutrophil function, such as increases in blood estradiol and cortisol concentrations around calving, and deficit in nutrients and minerals such as vitamins A and E, calcium, and selenium (Goff and Horst, 1997; Kimura et al., 2002; Hammon et al., 2006). Additionally, neutrophils from cows with retained placenta (RP) also have decreased migration ability and decreased myeloperoxidase activity (Kimura et al., 2002). Cows with the greatest influx of neutrophils into the uterus have reduced risk of bacterial infection and reduced incidence of endometritis (Gilbert et al., 2007). The migration of neutrophils into the mammary gland is also believed to play a role in clearance of mastitis pathogens (Paape et al., 2002). IL-8 is a chemoattractant for neutrophils; binding of IL-8 to its receptors (CXCR1 and CXCR2) in the neutrophil induces neutrophil activation, stimulates chemotaxis, and increases phagocytosis and killing ability (Mitchell et al., 2003). Because neutrophils play a role in the maintenance of endometrial health, an appropriate stimulus to selectively attract neutrophils into the uterus is believed to be needed. However, continued inflammation results in the development of chronic uterine disease, which impairs fertility and reduces dairy profitability (Dubuc et al., 2011; Lima et al., 2013). Therefore, the present invention provides a counter-intuitive approach to, in one aspect, provide therapy and/or prophylaxis of uterine conditions that are known to be positively correlated with inflammation by administering IL-8, which is also known to promote inflammation. In this regard, and without intending to be constrained by theory, we developed the present invention by exploring whether administration of IL-8 could, despite its pro-inflammatory properties, nevertheless recruit and activate neutrophils into the uterus, resulting in early influx of neutrophils into the uterine lumen, early detachment of the placenta, early bacterial contamination clearance, and ultimately a net positive result in the form of healthier more fertile dairy cows. As evidenced by the following Examples, administration of IL-8 does result in healthier and more fertile dairy cows, and unexpectedly improves their milk production and fat content of the milk.

The following Examples illustrate specific embodiments of the invention and are not intended to be limiting.

EXAMPLE 1

This Example provides a description of material and methods used to generate data described in Example 2.

Farm and Management

The study was conducted in a large commercial dairy farm located in Cayuga County near Ithaca, N.Y. The farm milked 3,300 Holstein cows 3 times daily in a double 52-stall parallel milking parlor. The cows were housed in freestall barns, with concrete stalls covered with mattresses and bedded with manure solids. All cows were offered a TMR consisting of approximately 55% forage (corn silage, haylage, and wheat straw) and 45% concentrate (corn meal, soybean meal, canola, cottonseed, and citrus pulp) on a DM basis. The diet was formulated to meet or exceed the NRC nutrient requirements for lactating Holstein cows weighing 650 kg and producing 45 kg of 3.5% FCM (NRC, 2001). The farm reproductive management used a combination of Presynch, Ovsynch, Resynch and detection of estrus, with 25 to 30% of cows bred via timed AI and the remainder bred after detection of estrus solely by activity monitors (Alpro; DeLaval, Kans. City, Mo.).

Study Design, Treatment and Sample Collection

A total of 217 fresh cows were enrolled in the study. Cows were blocked by parity and randomly allocated into one of 3 treatments: control, low dose IL-8 (L-IL8), and high dose IL-8 (H-IL8). Cows allocated in H-IL8 and L-IL8 received intrauterine infusion of 250 ml of saline containing 1,125 and 11.25 μg of recombinant IL-8, respectively. IL-8 was produced using the pET28-His-LEK-IL8 described above and consisted of the sequence of SEQ ID NO:1.

Control cows received intrauterine infusion of 250 ml of saline, as a placebo. All fresh cows that were available during the enrollment period were included in the study. Randomization was completed in Excel (Microsoft, Redmond, Wash.) using the random number function and imported into the farm's Dairy Comp 305 program (Valley Agricultural Software, Tulare, Calif.).

The treatments were administered no longer than 14 hours after parturition by the research team as follows: cows were restrained and the perineum area was cleansed and disinfected with 70% ethanol. Then, a sterile "Gilt" A.I. catheter (Livestock concepts, Hawarden) attached to a 250 ml saline bag was introduced to the cranial vagina. The catheter was manipulated into the uterus and the tip was exposed to uterine lumen and treatment was flushed inside the uterus. A swab was collected from the tip of the catheter; it was aerobically cultured on CHROMagar-*E. coli* (CHROMagar, Paris, France) at 37° C.

Milk and blood samples were collected from 60 cows (20 cows per treatment group) for the first four days of lactation. To obtain serum samples, blood was collected from a coccygeal vein/artery using a Vacutainer tube without anticoagulant and a 20 gauge 62.54 cm Vacutainer needle (Becton, Dickinson and Company, Franklin Lakes, N.J.). All blood samples were transported to the laboratory on ice and spun in a centrifuge at 2,000×g for 15 min at 4° C.; serum was harvested and frozen at −80° C.

Case Definitions

Retained placenta and metritis were diagnosed and treated by trained farm personnel according to specific protocols designed by the Ambulatory and Production Medicine Clinic at Cornell University. After parturition, cows were kept in the same pen until 20 DIM. This pen was monitored by farm employees, and cows were submitted to a complete physical exam if they were showing signs of dullness and depression; cows with fetid, watery, red brown uterine discharge accompanied with fever were diagnosed with puerperal metritis and treated by farm employees. Farm personnel were blinded to the treatments. Retained placenta was defined as a condition in which cows failed to release their fetal membranes within 24 h of calving.

Clinical endometritis evaluation was performed by the investigators at 35±3 DIM, and it was defined as a presence of purulent or mucopurulent discharge, by retrieving vaginal mucus using the Metricheck device (Metricheck, Simcro-Tech, Hamilton, New Zealand). The vaginal discharge was scored using a modified 0 to 5 scale (0=no secretion material retrieved, 1=clear mucus, 2=flecks of pus in the vaginal discharge, 3=<50% of pus in the vaginal discharge, 4=>50% of pus in the vaginal discharge, 5=watery, fetid vaginal discharge). Cows that had score≥3 were considered to have clinical endometritis.

Rectal temperature was measured at enrollment, 3, 6, and 9 DIM using a digital thermometer (GLA M750, GLA Agriculture Electronics, CA) equipped with an angle probe (11.5 cm, 42o). Body condition scores were recorded at enrollment and 35 DIM by a single investigator using a 5-point scale with a quarter-point system, as previously described (Edmonson et al., 1989). Body condition score loss was defined as the difference between BCS at enrollment and at 35 DIM.

Data regarding calf (female, male, twins, and stillbirth), assisted parturition, days of gestation at parturition, milk production and somatic cell counts were extracted from the farm's DairyComp 305 database (Valley Agricultural Software, Tulare, Calif.).

Blood and Milk Parameters

The IL-8 concentrations of serum and milk samples were determined using a human IL-8 ELISA kit (R&D Systems Inc., Minneapolis, Minn.) validated for use in cattle. Serum samples were also tested for BHBA concentrations using an electronic BHBA measuring system (Precision Xtra, Abbott, Abingdon, UK) already validated for animal use. Cows that were tested with over 1.2 μmol/L of BHBA in at least one of the first four days of lactation were considered as having subclinical ketosis. Serum glucose levels were measured using a portable glucometer (Accu-Check Active, Roche Diagnostics, Indianapolis, Ind.). The serum IGF-1 levels were determined using a human IGF-1 ELISA kit (R&D Systems Inc., Minneapolis, Minn.).

Serum haptoglobin concentration was determined using a colorimetric procedure that measures haptoglobin/hemoglobin complex by estimated differences in peroxidase activity. Briefly, 5 μL of plasma or distillated water (for blank determination) was added to 7.5 mL of 0-dianisidine solution (0.6 g/L of O-dianisidine, 0.5 g/L of EDTA, and 13.8 g/L of sodium phosphate monobasic in distilled water; pH adjusted to 4.1) in a borosilicate tube. Twenty-five microliters of a hemoglobin solution (0.3 g/L of bovine hemoglobin in distilled water) was immediately added to each tube. All tubes were incubated in a water bath set at 37° C. for 45 min. After incubation, 100 μL of a freshly prepared working concentration of 156 mM hydrogen peroxide solution was added to each tube. All tubes were incubated for 1 h at room temperature. After incubation, 200 μL of each tube was transferred into one well in a 96-well polystyrene flat-bottom microplate, and optical density (OD) was immediately read at 450 nm in a microplate reader (BioTek Instruments, Model EL 340, Winooski, Vt.). The OD from the blank sample was subtracted from the OD of all plasma-containing samples. Results were reported as optical density readings at 450 nm of wavelength, given that the method that was used does not contain a standard curve.

Statistical Analysis

Descriptive statistics analyses were undertaken in JMP®PRO 10, using the ANOVA and chi-square functions for continuous and categorical data, respectively. Ten mixed general linear models were fitted to the data using the MIXED procedure of SAS (SAS Institute). The dependent variables evaluated in this study were: average daily milk production (kg/d), average fat corrected milk production (kg/d), average daily energy corrected milk (kg/d), SCC linear score, blood BHBA concentration (μmol/L), blood IL-8 concentration (pg/ml), blood haptoglobin, blood IGF-1 concentration (ng/ml), serum glucose concentration (mg/dL), and rectal temperature (° C.). The data comprised a series of repeated measures of each dependent variable, throughout the first eight weeks of lactation for average daily milk production; the first two months of lactation for average fat corrected milk production, average daily energy corrected milk, and SCC linear score; the first four days of lactation for blood BHBA concentration, blood IL-8 concentration, blood haptoglobin, blood IGF-1, and serum glucose concentration; and 3, 6, and 9 days post-partum for rectal temperature. To account appropriately for within-cow correlation, the error term was modeled by imposing a first-order autoregressive covariance structure for all statistical models (which assumed the within-cow correlation of the repeated measures). The independent variables offered to the models were: treatment, parity, placenta presence at enrollment, E. coli intrauterine culture outcome, assisted parturition, calf, body condition score at parturition, days of gestation at parturition, temperature at enrollment, and time of data collection. Biologically plausible two-way and three-way interactions were offered to the models. Furthermore, variables and their respective interaction terms in all models were retained in the model when P-value<0.10. The variable treatment was forced into all models.

To evaluate the effect of treatment on the odds of puerperal metritis, clinical endometritis, and subclinical ketosis, three mixed logistic regressions were fitted to the data using the GLIMMIX procedure of SAS. The models included the fixed effects of treatment, parity, placenta presence at enrollment, E. coli intrauterine culture outcome, assisted parturition, calf, body condition score at parturition, days of gestation at parturition, and temperature at enrollment. Biologically plausible two-way and three-way interactions were offered to the models. Moreover, variables and their respective interaction terms in all models were retained in the model when P-value<0.10. The variable treatment, parity, and the interaction term between parity and treatment were forced into all models. To obtain strata-specific odds ratio parameters for the different concentrations of the interaction term between parity and treatment, the lsmeans option of the GLIMMIX procedure (binary distribution) was used. P-values were adjusted for multiple comparisons using the Tukey's HSD test. To assess the proportion of cows that had detectable levels of IL-8 in milk samples, and the incidences of puerperal metritis, clinical endometritis, and subclinical ketosis, the chi-square function in JMP®PRO 10 was used.

EXAMPLE 2

This Example provides results obtained using the materials and methods described in Example 1.

Descriptive statistics regarding number of multiparous and primiparous animals enrolled, number of enrolled animals that were positive for intrauterine E. coli culture, number of enrolled animals with placenta present at enrollment, number of enrolled animals that had assisted parturition, number of enrolled animals that calved a female, male, twins or stillborn calves, average days of gestation at parturition, average body condition score at parturition, and average rectal temperature at enrollment are presented in Table 1.

TABLE 1

Descriptive statistics of the 213 study cows enrolled in three treatment groups.

|  | Control | IL-8 (11.25 µg) | IL-8 (1125.00 µg) | P-value |
|---|---|---|---|---|
| Enrolled primiparous cows (%) | 32 (48) | 41 (51) | 31 (47) | 0.86 |
| Enrolled multiparous cows (%) | 35 (52) | 39 (49) | 35 (53) |  |
| Total | 67 | 80 | 66 |  |
| Enrolled cows with positive intrauterine E. coli outcome (%) | 42 (63) | 39 (49) | 30 (45) | 0.10 |
| Cows with placenta present at enrollment (%) | 21 (31) | 23 (29) | 27 (41) | 0.28 |
| Enrolled cows with assisted parturition | 2 (3) | 3 (4) | 1 (2) | 0.71 |
| Enrolled cows that calved a female calf (%) | 37 (55) | 38 (48) | 37 (56) | 0.28 |
| Enrolled cows that calved a male calf (%) | 23 (34) | 37 (46) | 25 (38) |  |
| Enrolled cows that had twin parturition (%) | 4 (5) | 0 (0) | 2 (3) |  |
| Enrolled cows that had stillbirth parturition (%) | 3 (6) | 5 (6) | 2 (3) |  |
| Average days of gestation at parturition | 274.9 | 277.4 | 275.2 | 0.06 |
| Average BCS at parturition | 3.36 | 3.41 | 3.40 | 0.42 |
| Average rectal temperature at enrollment | 38.7 | 38.8 | 38.8 | 0.59 |
| Total enrolled animals (%) | 67 (31) | 80 (38) | 66 (31) |  |

The effect of treatment on milk production by week of lactation for primiparous and multiparous cows is presented in FIG. 1. The overall milk production was greater for IL-8 treated cows; 33.1 kg/d (95% CI=32.0-34.2), 35.6 kg/d (95% CI=34.5-36.7), and 35.9 kg/d (95% CI=34.9-37.0) for control, L-IL8, and H-IL8 cows, respectively (P-value<0.01). The variables parity, calf, average days of gestation at parturition, rectal temperature at enrollment, and week of lactation were retained in the model. The interaction between treatment and week of lactation was not significant (P-value=0.06).

Figure 2:
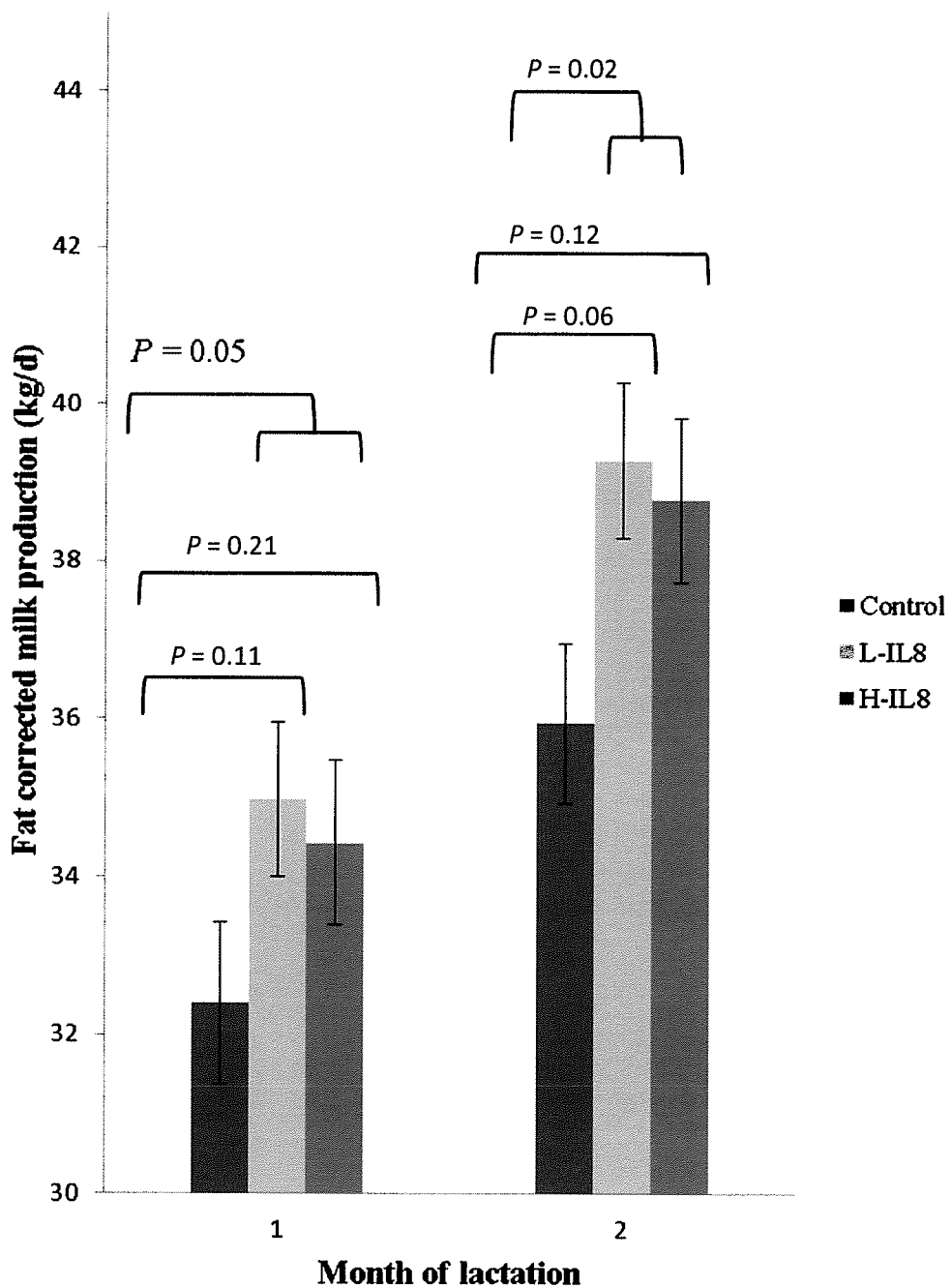
FIG. 2: Fat corrected milk production (kg/d) during the first two months of lactation. The overall fat corrected milk production was higher for L-IL8, and H-IL8 cows than for control cows (P-value=0.02). The interaction between treatment and month of lactation was not significant (P-value=0.89). The error bars stand for the standard error of the mean.

The effect of treatment on fat corrected milk production for the first two months of lactation is presented in FIG. 2. The overall fat corrected milk production was higher for IL-8 treated cows; 34.2 kg/d (95% CI=32.6-35.7), 37.1 kg/d (95% CI=35.7-38.5), and 36.6 kg/d (95% CI=35.0-38.1) for control, L-IL8, and H-IL8 cows, respectively (P-value=0.02). The variables parity, body condition score at parturition, average days of gestation at parturition, rectal temperature at enrollment, and month of lactation were retained in the model. The interaction between treatment and month of lactation was not significant (P-value=0.89).

Figure 3:
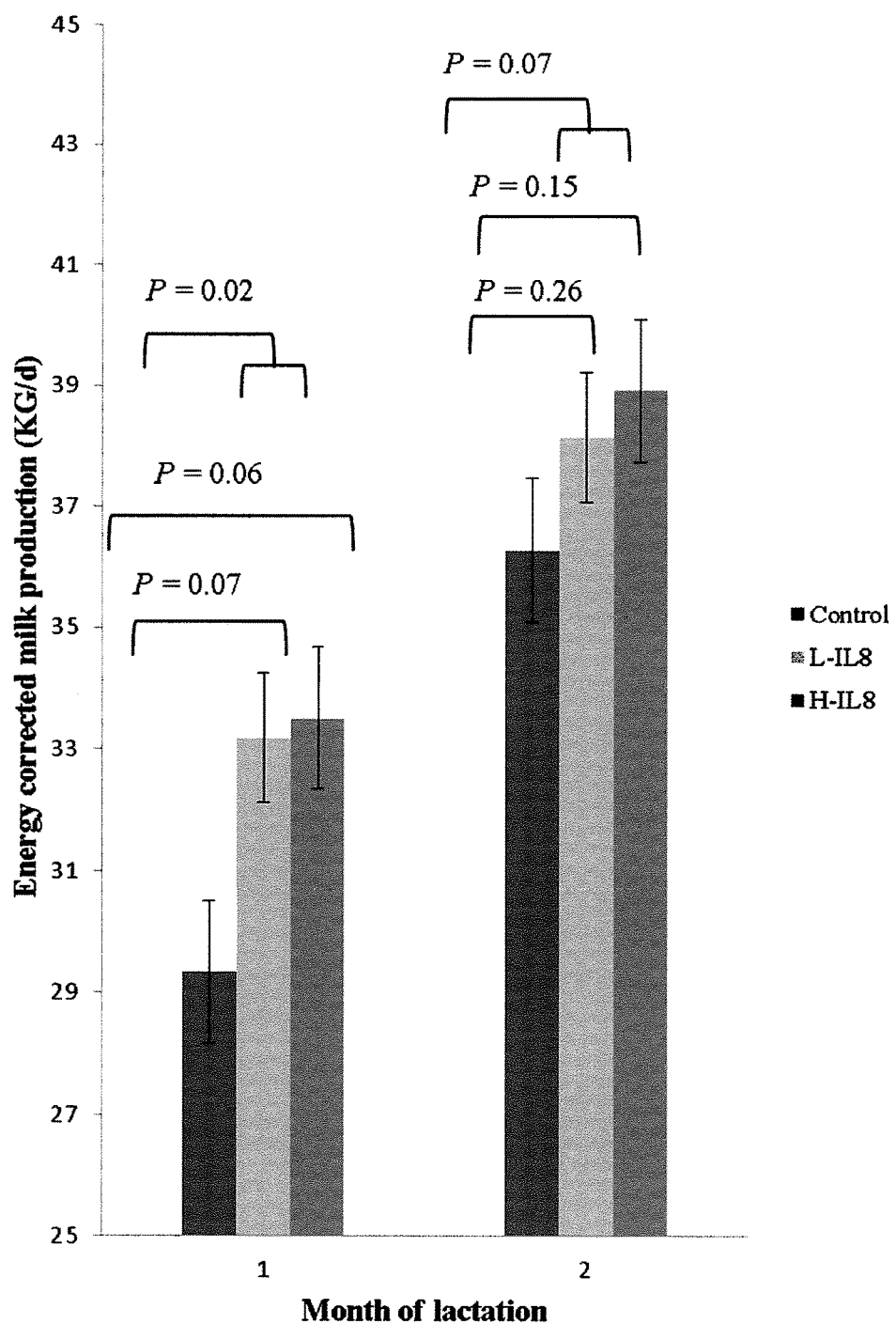
FIG. 3: Energy corrected milk production (kg/d) during the first two months of lactation. The overall energy corrected milk production was higher for L-IL8 and H-IL8 cows, compared to control counterparts (P-value=0.02). The interaction between treatment and month of lactation was not significant (P-value=0.56). The error bars stand for the standard error of the mean.

The effect of treatment on energy corrected milk production during the first two months of lactation is presented in FIG. 3. The overall energy corrected milk production was higher for IL-8 treated cows; 32.8 kg/d (95% CI=30.9-34.6), 35.7 kg/d (95% CI=34.0-37.3), and 36.2 kg/d (95% CI=34.3-38.1) for control, L-IL8, and H-IL8 cows, respectively (P-value=0.02). The variables parity, body condition score at parturition, average days of gestation at parturition, and month of lactation were retained in the model. The interaction between treatment and month of lactation was not significant (P-value=0.56).

Figure 4:
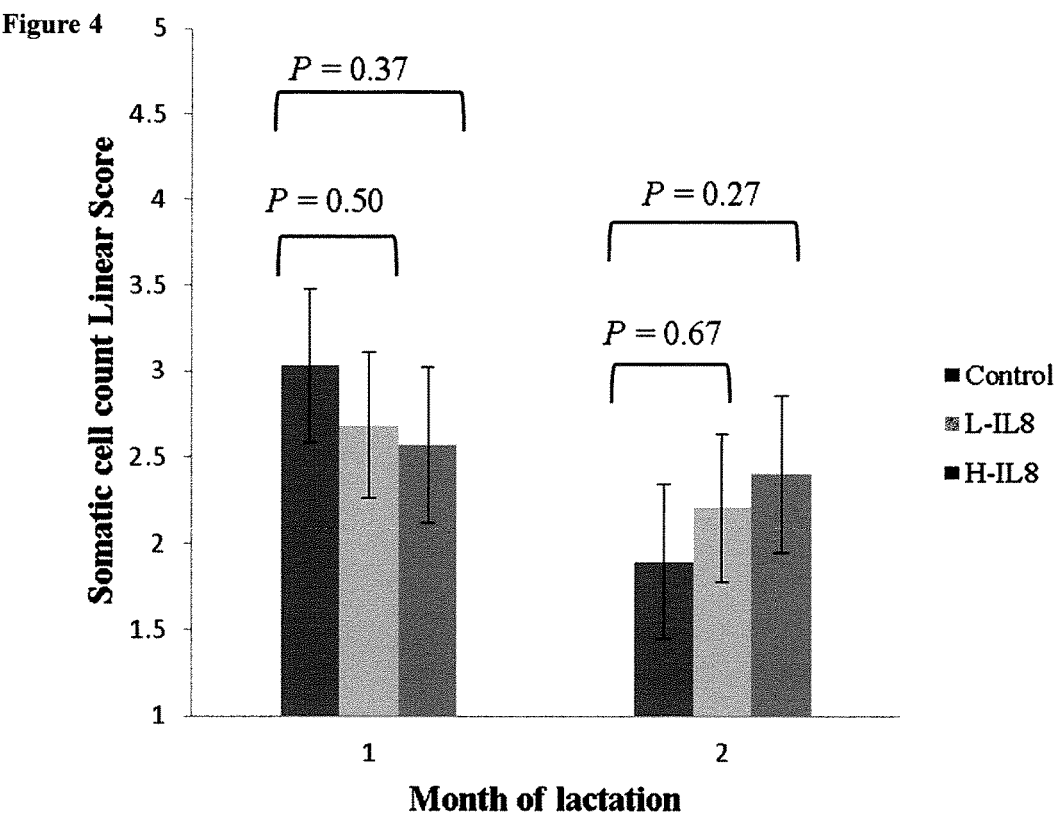
FIG. 4: Somatic cell count linear score during the first two months of lactation. The overall somatic cell count linear score was not affected by treatment (P-value=0.02). The interaction between treatment and month of lactation was not significant (P-value=0.09). The error bars stand for the standard error of the mean.

The effect of treatment on SCC linear score during the first two months of lactation is presented in FIG. 4. The overall somatic cell count linear score was not different between treatment groups; 2.46 (95% CI=1.64-3.28), 2.44 (95% CI=1.66-3.23), and 2.48 (95% CI=1.65-3.31) for control, L-IL8, and H-IL8 cows, respectively (P-value=0.99). The variables assisted parturition and month of lactation were retained in the model. The interaction between treatment and month of lactation was not significant (P-value=0.09).

Figure 5:
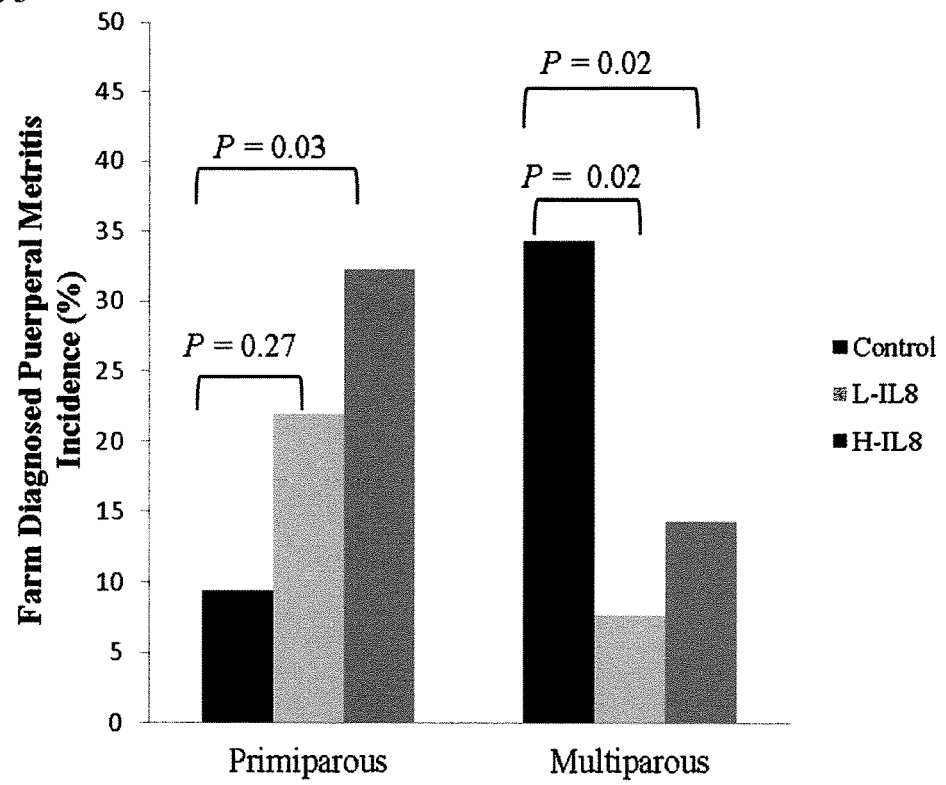
FIG. 5: The effect of treatment on the farm diagnosed puerperal metritis incidence on primiparous and multiparous cows.
Figure 6:
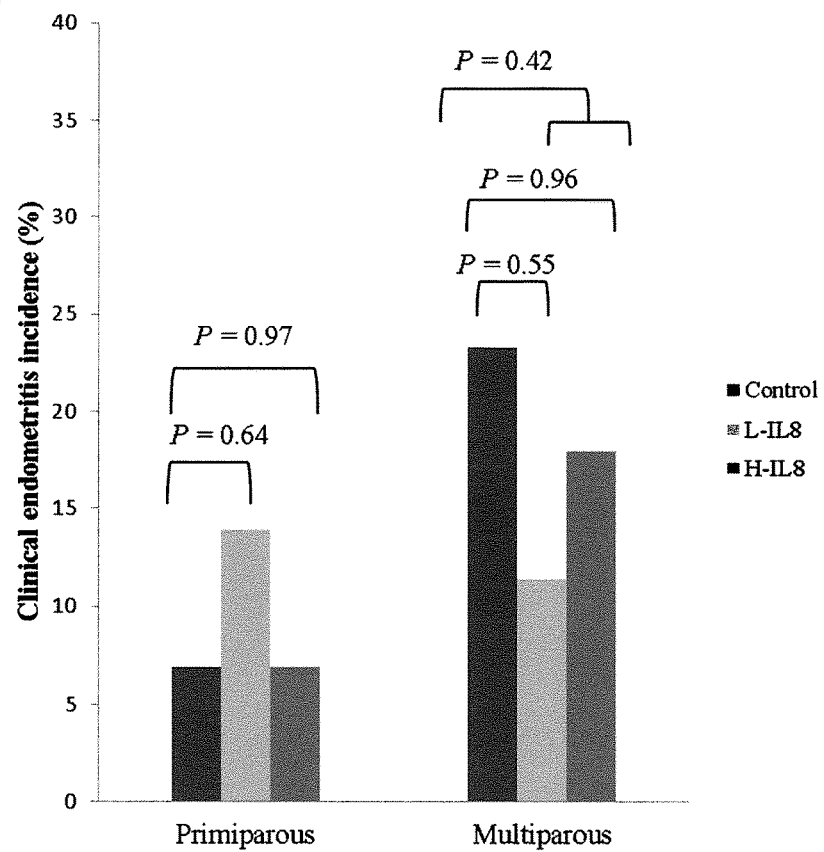
FIG. 6: The effect of treatment on the clinical endometritis incidence on primiparous and multiparous cows.

The effect of treatment on farm diagnosed puerperal metritis incidence was dependent on parity, and is presented in FIG. 5; the interaction between treatment and parity was significant (P-value<0.01). For primiparous animals, H-IL8 cows were at 7.43 higher odds of having puerperal metritis compared to control cows (P-value=0.03), while the odds of having puerperal metritis for L-IL8 and control cows were not different (P-value=0.27). On the other hand, for multiparous animals, intrauterine IL-8 treatment had a protective effect against puerperal metritis; control cows were at 7.14 (P-value=0.02) and 5.88 (P-value=0.02) increased odds of having puerperal metritis than L-IL8 and H-IL8 cows, respectively. In one non-limiting embodiment the disclosure relates to prophylaxis of puerperal metritis in multiparous animals. The effect of treatment on clinical endometritis incidence is presented in FIG. 6. Intrauterine infusion of IL-8 was not protective against clinical endometritis. (P-value=0.73).

Figure 7:
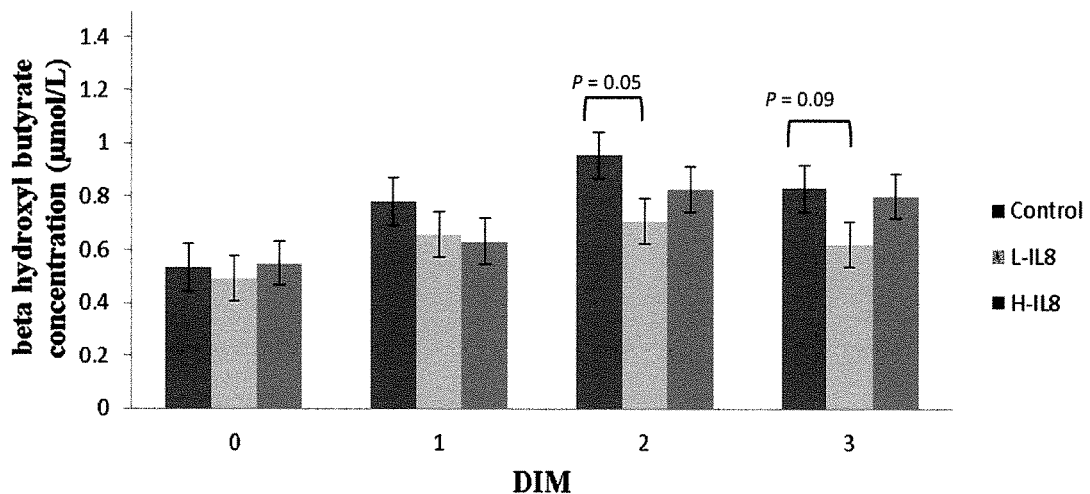
FIG. 7: Blood beta hydroxyl butyrate (BHBA) concentration by DIM. The overall blood BHBA concentration was 077 µmol/L (95% CI=0.65-0.90), 0.62 µmol/L (95% CI=0.50-0.74), and 70 µmol/L (95% CI=0.58-0.82) for control, L-IL8, and H-IL8 cows, respectively (P-value=0.22). The interaction between treatment and DIM was not significant (P-value=0.66). The error bars stand for the standard error of the mean.

The overall blood BHBA concentration was 0.77 μmol/L (95% CI=0.65-0.90), 0.62 μmol/L (95% CI=0.50-0.74), and 70 μmol/L (95% CI=0.58-0.82) for control, L-IL8, and H-IL8 cows, respectively (P-value=0.22). Additionally, the interaction between treatment and DIM was not significant (P-value=0.66, FIG. 7).

Figure 8:
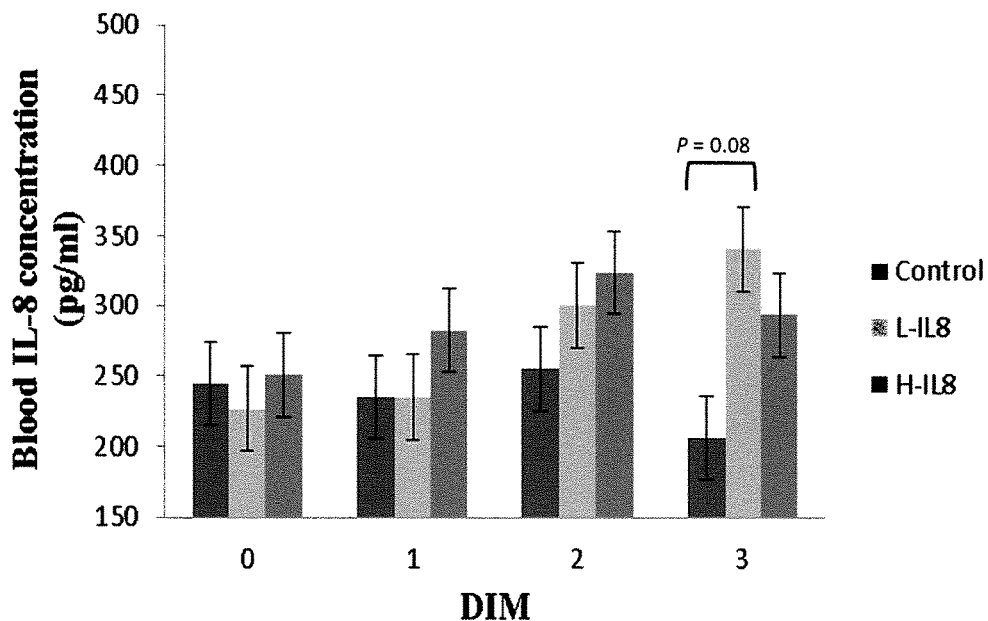
FIG. 8: Blood IL-8 concentration by DIM. The overall blood IL-8 concentration was not increased by IL-8 intrauterine infusion (P-value=0.17). The interaction between treatment and DIM was not significant (P-value=0.16). The error bars stand for the standard error of the mean.

The overall blood IL-8 concentration was 235.0 pg/ml (95% CI=193.9-276.0), 275.5 pg/ml (95% CI=233.7-317.4), and 287.5 pg/ml (95% CI=246.0-329.0) for control, L-IL8, and H-IL8 cows, respectively (P-value=0.17, FIG. 8). The variables rectal temperature at enrollment and DIM were retained in the model. The interaction between treatment and DIM was not significant (P-value=0.16).

Most of milk samples tested for IL-8 concentration had levels below the detection limit of the assay used (1.5 pg/ml). From all the 182 samples tested, only 13.7% (25 samples) had IL-8 concentration above the detection limit. Therefore, very little inference can be made regarding the effect of intrauterine infusion of IL-8 on milk concentration of this cytokine. The proportion of samples collected prior to treatment that had IL-8 concentrations above the detection limit was 40.0%, 43.0%, and 23.5% for control, L-IL8, and H-IL8, respectively (P-value=0.10). The proportion of samples collected after treatment that had IL-8 levels above the detection limit of the assay was 2.2%, 20.0%, and 0.0%, for control, L-IL8, and H-IL8, respectively (P-value<0.01).

Figure 9:
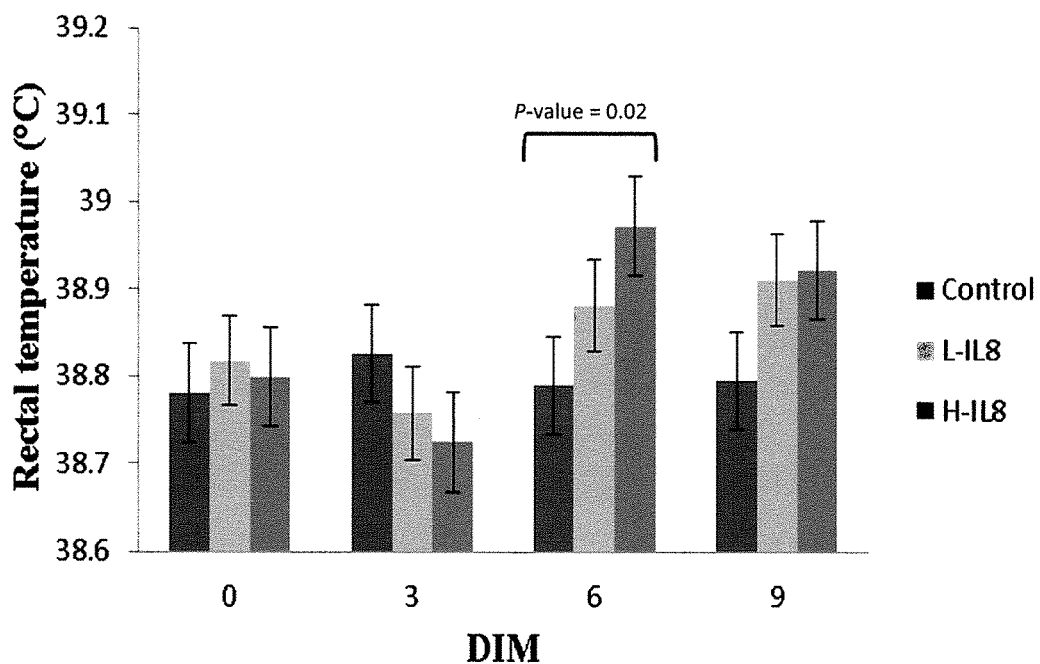
FIG. 9: Rectal temperature by DIM. The overall rectal temperature was not different between treatment groups (P-value=0.47). The interaction between treatment and DIM was not significant (P-value=0.13). The error bars stand for the standard error of the mean.

The overall rectal temperature was 38.8° C. (95% CI=38.7-38.9), 38.8° C. (95% CI=38.8-38.9), and 38.8° C. (95% CI=38.8-38.9) for control, L-IL8, and H-IL8 cows, respectively (P-value=0.47, FIG. 9). The variables placenta at enrollment, body condition score at parturition, days of gestation at parturition, and DIM were retained in the model. The interaction between treatment and DIM was not significant (P-value=0.13). At 6 DIM, control cows had lower rectal temperature compared to H-IL8 cows (P-value=0.02).

Figure 10:
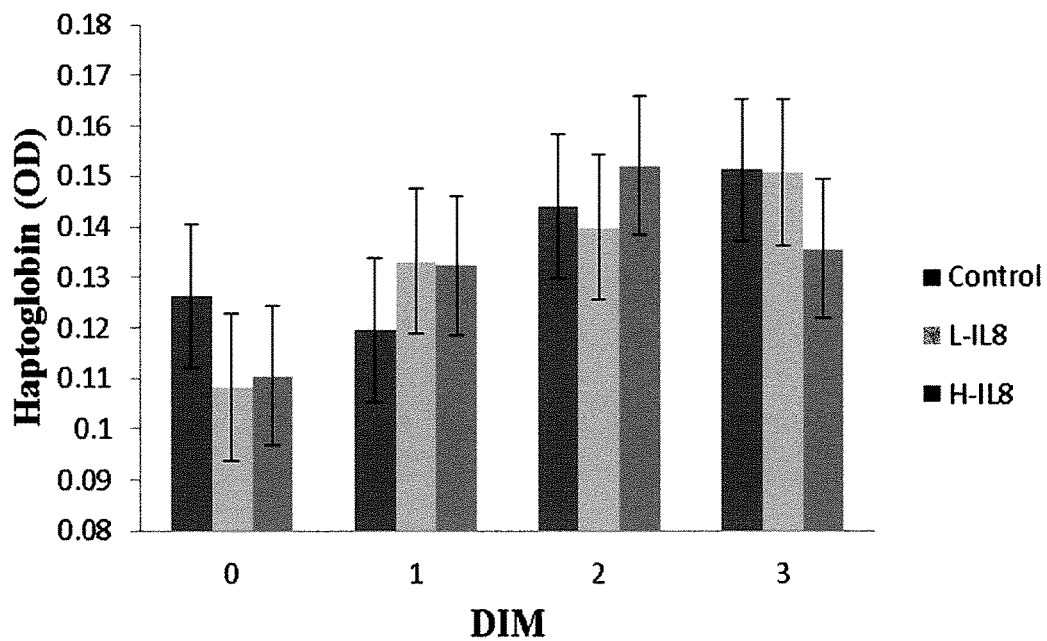
FIG. 10: Blood haptoglobin levels by DIM. The overall blood haptoglobin level was not increased by IL-8 intrauterine infusion (P-value=0.96). The interaction between treatment and DIM was not significant (P-value=0.48). The error bars stand for the standard error of the mean.

Haptoglobin levels during the first four days after parturition was not influenced by treatment (FIG. 10); the overall haptoglobin level was 0.13 (95% CI=0.11-0.16), 0.13 (95% CI=0.11-0.16), and 0.13 (95% CI=0.11-0.15) for control, L-IL8, and H-IL8 cows, respectively (P-value=0.96). The variables parity, calf, and DIM were retained in the model. The interaction between treatment and DIM was not significant (P-value=0.48).

Figure 11:
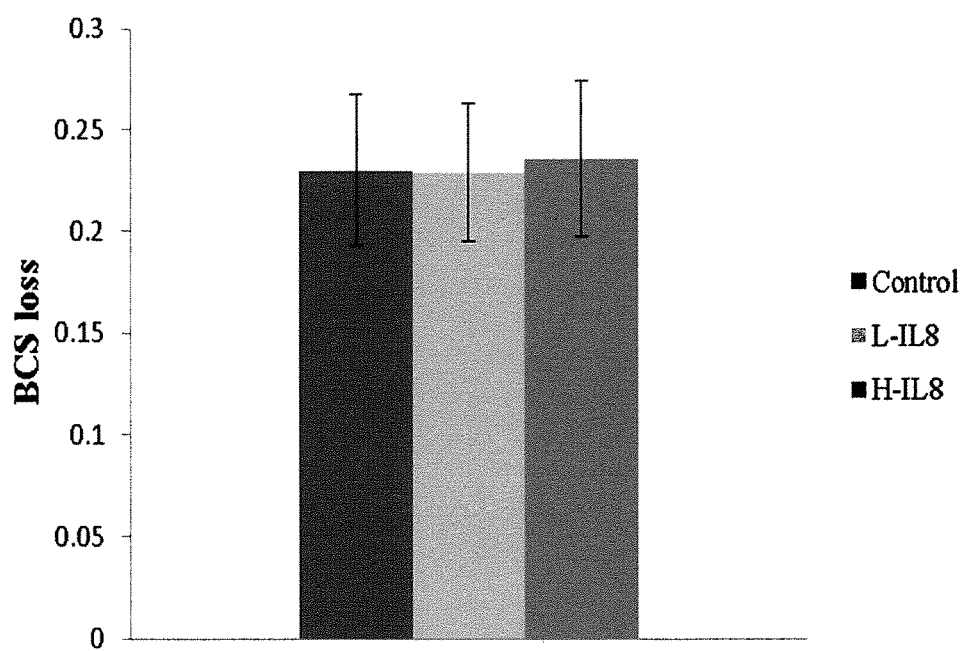
FIG. 11: Body condition score loss from day of parturition until 35 DIM was not affected by treatment (P-value=0.99).

Treatment did not have an effect on body condition score loss from day of parturition to 35 DIM (FIG. 11). The average body condition score loss was 0.23 (95% CI=0.15-0.30), 0.23 (95% CI=0.16-0.30), and 0.23 (95% CI=0.16-0.31) for control, L-IL8, and H-IL8 cows, respectively (P-value=0.99). The variable parity was retained in the model.

Figure 12:
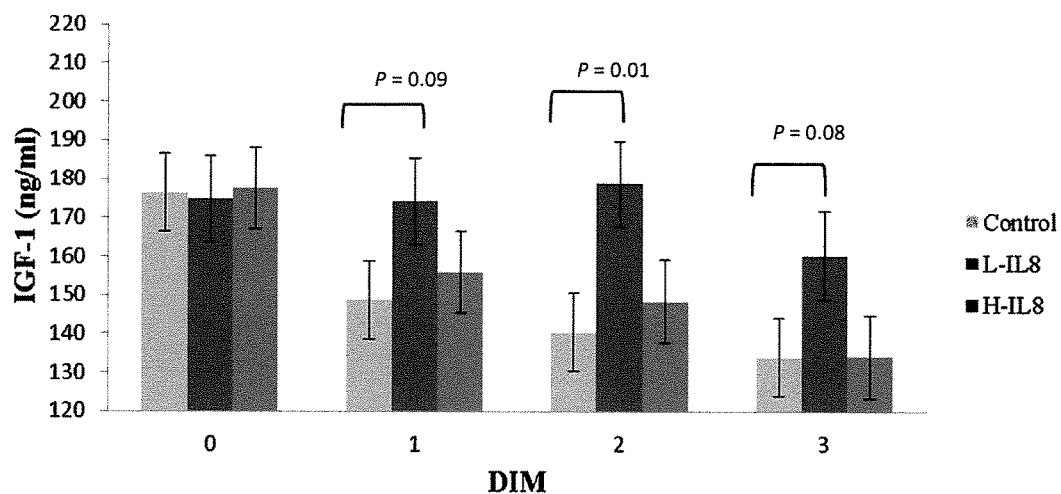
FIG. 12: Blood IGF-1 levels by DIM. The overall blood IGF-1 level was not increased by IL-8 intrauterine infusion (P-value=0.18). The interaction between treatment and DIM was not significant (P-value=0.25). The error bars stand for the standard error of the mean.

The overall IGF-1 serum levels was 149.9 ng/ml (95% CI=133.2-166.5), 172.0 ng/ml (95% CI=153.6-190.4), and 153.9 ng/ml (95% CI=136.5-171.4) for control, L-IL8, and H-IL8 cows, respectively (P-value=0.18, FIG. 12). The variable DIM was retained in the model. The interaction between treatment and DIM was not significant (P-value=0.25). However, L-IL8 cows had or tended to have greater blood IGF-1 levels on days 1 (P-value=0.09), 2 (P-value=0.01), and 3 (P-value=0.08) postpartum.

Figure 13:
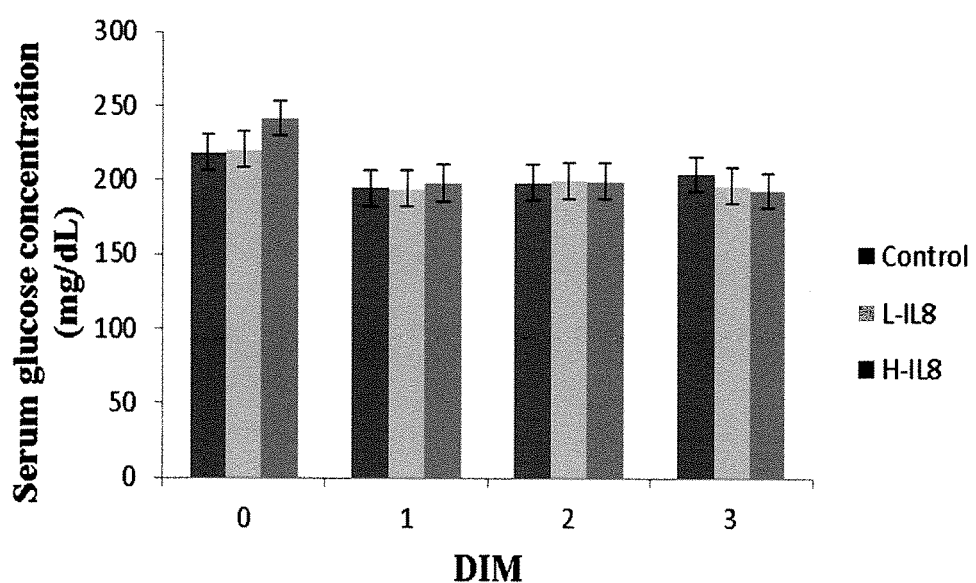
FIG. 13: Serum glucose concentration by DIM. The overall serum glucose concentration was not increased by IL-8 intrauterine infusion (P-value=0.10). The interaction between treatment and DIM was not significant (P-value=0.55). The error bars stand for the standard error of the mean.

The overall serum glucose concentration was 218.5 mg/dl (95% CI=195.2-241.8), 220.5 mg/dl (95% CI=196.7-244.3), and 241.6 mg/dl (95% CI=218.6-264.5) for control, L-IL8, and H-IL8 cows, respectively (P-value=0.11, FIG. 13). The variables parity, calf, and DIM were retained in the model. The interaction between treatment and DIM was not significant (P-value=0.53).

Figure 14:
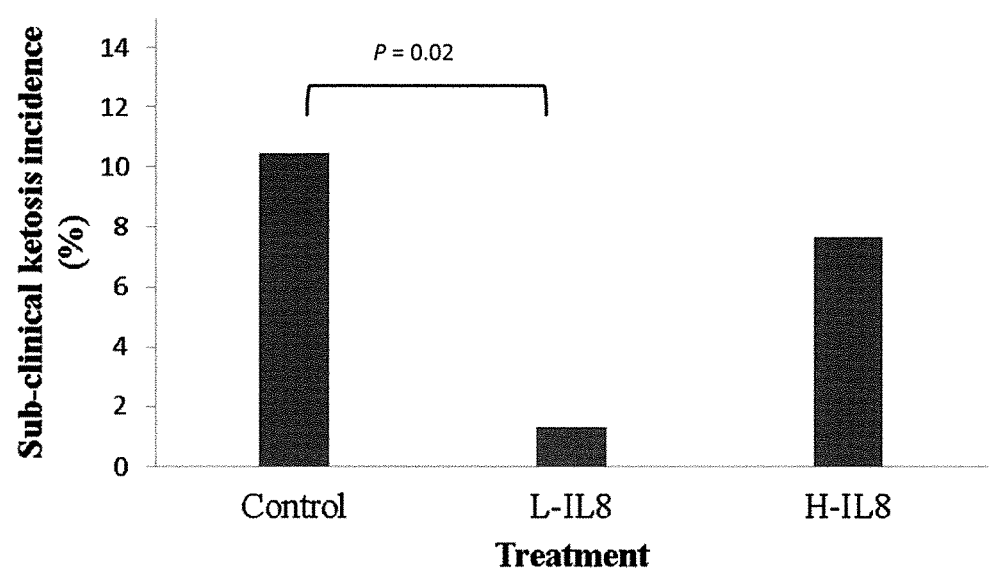
FIG. 14: The effect of treatment on the sub-clinical ketosis incidence.

The effect of treatment on subclinical ketosis incidence is presented in FIG. 14. L-IL8 treatment had a protective effect against subclinical ketosis; control cows were at 8.04 increased odds of having subclinical ketosis than L-IL8 cows (P-value=0.02). However, the incidence of subclinical ketosis was not different between control and H-IL8 cows (P-value=0.30).

EXAMPLE 3

Figure 16:
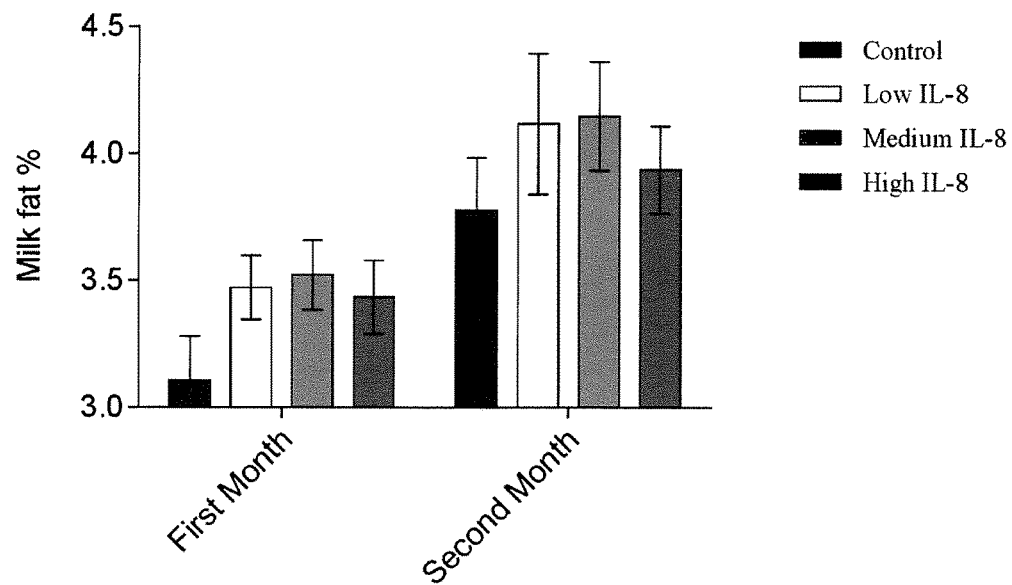
FIG. 16: Effect of the different intra-uterine IL-8 treatment doses on the percent of milk fat at the first and second months of lactation. The bars are shown for the First Month and the Second Month from left to right as Control, Low IL-8, Medium IL-8, and High IL-8.
Figure 17:
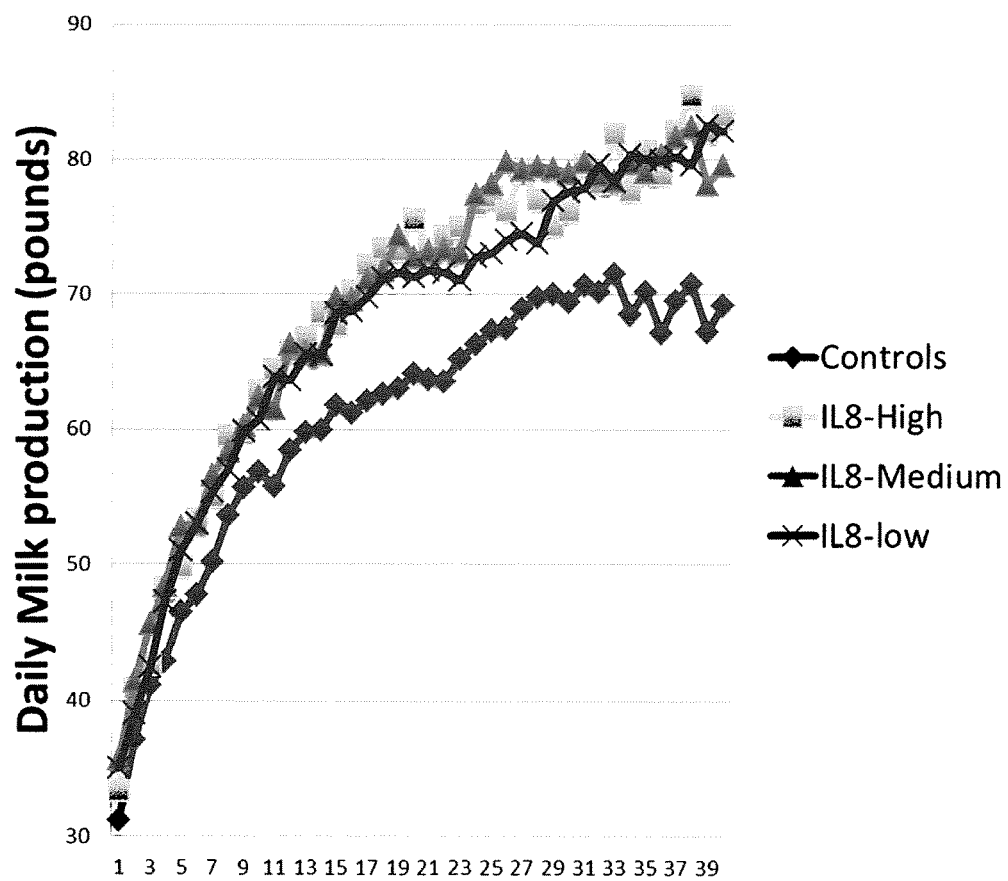
FIG. 17: Effect of the different intra-uterine IL-8 treatment doses on daily milk production.
Figure 18:
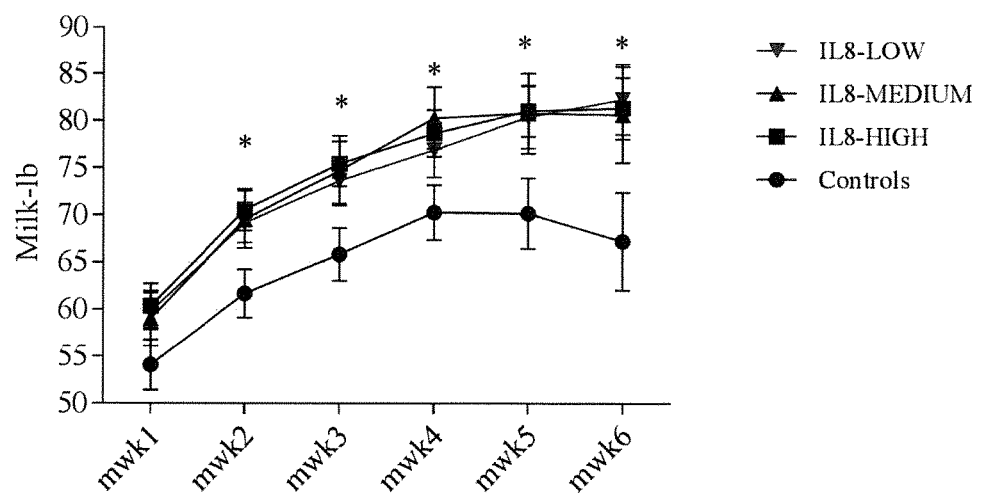
FIG. 18: Effect of the different intra-uterine IL-8 treatment doses on weekly milk production.
Figure 19:
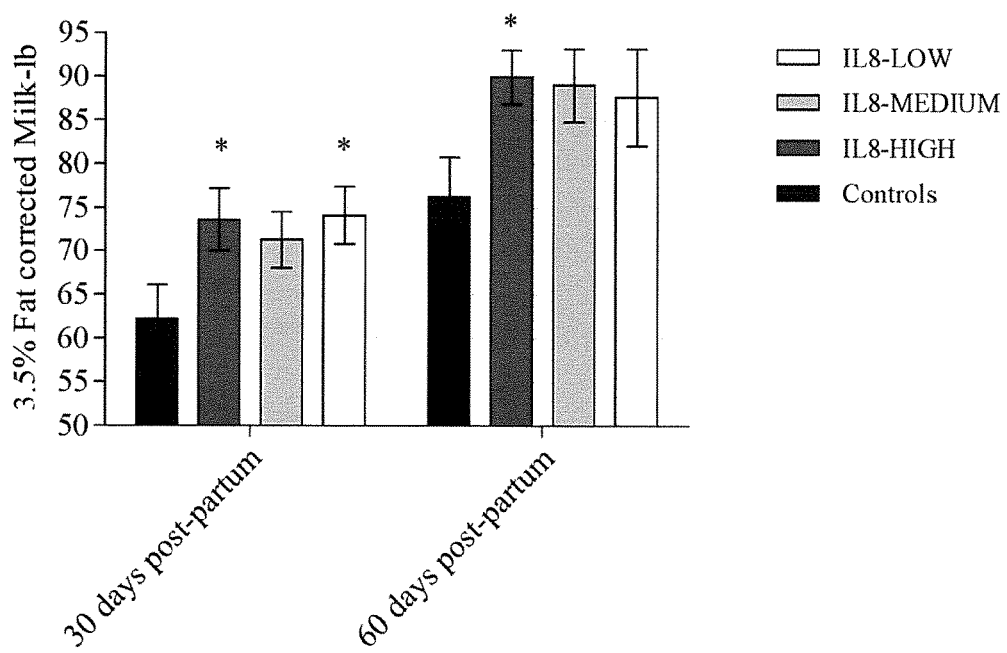
FIG. 19: Effect of the different intra-uterine IL-8 treatment doses on 3.5% fat corrected milk. The bars are shown from left to right as Control, IL8-HIGH, IL8 MEDIUM, and IL8-LOW
Figure 20:
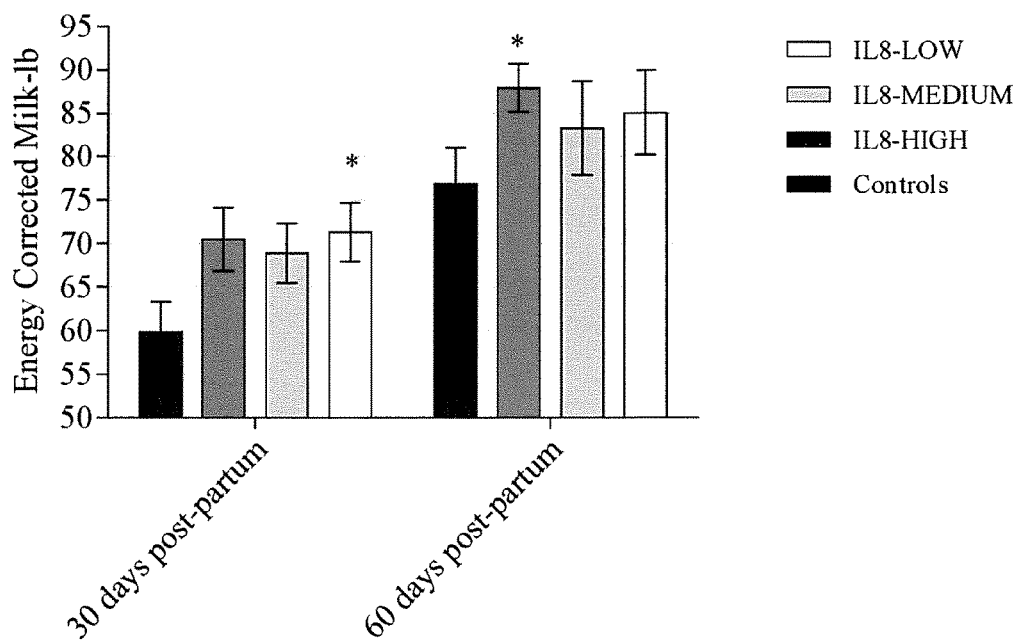
FIG. 20: Effect of the different intra-uterine IL-8 treatment doses on energy corrected milk. The bars are shown from left to right as Control, IL8-HIGH, IL-8-MEDIUM, and IL-8 LOW.

This Example reproduces the approach described in Examples 1 and 2 above, and further demonstrates that a wider range rIL-8 dosage is effective for improving milk production and milk content. The study was also conducted in a commercial dairy farm located in Cayuga, N.Y. A total of 341 fresh cows were enrolled in the study for 116 days. Within 12 hours of parturition, cows were randomly assigned to receive an intrauterine infusion with 9.5 mg of rIL-8 (High IL-8; n=86), 0.095 mg of rIL-8 (Medium IL-8; n=82), 0.0095 mg of rIL8 (Low IL8; n=88), or receive no treatment (Control; n=85). Postpartum cows were treated within 12 hours after parturition. Cows were restrained in headlock stations and had their perineal area disinfected with ethanol (70% v/v). A sterile gilt artificial insemination catheter (Livestock Concepts Inc., Hawarden, IA) attached to a 250 mL saline bag, that contained the respective dose of rIL8, was introduced to the cranial vagina, manipulated through the cervix, and the treatments were infused into the uterine lumen. Milk production was recorded on a daily basis and on monthly basis milk samples were submitted to the laboratory (DairyOne, Ithaca, N.Y.) for milk components evaluation (protein and milk fat). Energy corrected and 3.5% fat corrected milk were calculated and are reported here.

rIL8 treatment increased milk fat percentage regardless of treatment dose (FIG. 16). rIL8 treatment also increased daily milk yield (FIG. 17), weekly milk yield (FIG. 18), 3.5% fat corrected milk (FIG. 19), and energy corrected milk (FIG. 20). The results are in agreement with the results obtained from the experiments described in Examples 1 and 2, and show that cows treated with rIL8 produced on average 10 pounds more milk per day when compared to control.

EXAMPLE 4

Figure 21:
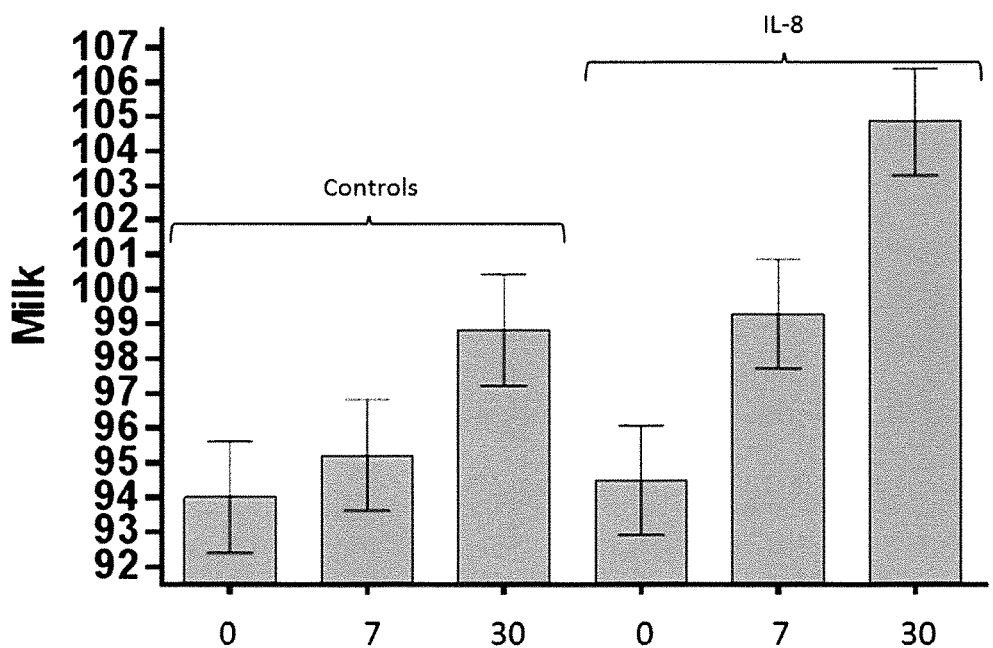
FIG. 21: Graphical representation of data showing intravaginal IL-8 administration significantly increases milk production. IL-8 was administered on day 0.

This Example demonstrates intravaginal IL-8 administration. To obtain the data summarized in FIG. 21, a total of 60 cows were randomly allocated to receive a placebo treatment (sterile saline; n=30) or 1.125 mg of rIL-8 (n=30). Treatments and placebos were administered intravaginaly. Enrolled cows were between 30-80 days post parturition (late lactation). As can be seen from FIG. 21, intravaginal IL-8 treatment significantly increased milk production.

While the invention has been described through specific embodiments, routine modifications will be apparent to those skilled in the art and such modifications are intended to be within the scope of the present invention.

SOURCES

Cai, T. Q., P. G. Weston, L. A. Lund, B. Brodie, D. J. McKenna and W. C. Wagner. 1994. Association between neutrophil functions and periparturient disorders in cows. Am. J. Vet. Res. 55:934-943.

Drackley, J. K. 1999. ADSA foundation scholar award. biology of dairy cows during the transition period: The final frontier? J. Dairy Sci. 82:2259-2273.

Dubuc, J., T. F. Duffield, K. E. Leslie, J. S. Walton and S. J. Leblanc. 2011. Randomized clinical trial of antibiotic and prostaglandin treatments for uterine health and reproductive performance in dairy cows. J. Dairy Sci. 94:1325-1338.

Edmonson, A. J., I. J. Lean, L. D. Weaver, T. Farver, and G. Webster. 1989. A body condition scoring chart of Holstein dairy cows. J. Dairy Sci. 72:68-78.

Galvao, K. N., M. J. Flaminio, S. B. Brittin, R. Sper, M. Fraga, L. Caixeta, A. Ricci, C. L. Guard, W. R. Butler and R. O. Gilbert. 2010. Association between uterine disease and indicators of neutrophil and systemic energy status in lactating holstein cows. J. Dairy Sci. 93:2926-2937.

Gilbert, R. O., S. T. Shin, C. L. Guard, H. N. Erb and M. Frajblat. 2005. Prevalence of endometritis and its effects on reproductive performance of dairy cows. Theriogenology. 64:1879-1888.

Goff, J. P. and R. L. Horst. 1997. Physiological changes at parturition and their relationship to metabolic disorders. J. Dairy Sci. 80:1260-1268.

Hammon, D. S., I. M. Evj en, T. R. Dhiman, J. P. Goff and J. L. Walters. 2006. Neutrophil function and energy status in holstein cows with uterine health disorders. Vet. Immunol. Immunopathol. 113:21-29.

Hussain, A. M. 1989. Bovine uterine defense mechanisms: A review. Zentralbl. Veterinarmed. B. 36:641-651.

Kehrli, M. E., Jr and J. P. Goff 1989. Periparturient hypocalcemia in cows: Effects on peripheral blood neutrophil and lymphocyte function. J. Dairy Sci. 72:1188-1196.

Kimura, K., J. P. Goff and M. E. Kehrli Jr. 1999. Effects of the presence of the mammary gland on expression of neutrophil adhesion molecules and myeloperoxidase activity in periparturient dairy cows. J. Dairy Sci. 82:2385-2392.

Kimura, K., J. P. Goff, M. E. Kehrli Jr and T. A. Reinhardt. 2002. Decreased neutrophil function as a cause of retained placenta in dairy cattle. J. Dairy Sci. 85:544-550.

Ley, K., J. B. Baker, M. I. Cybulsky, M. A. Gimbrone Jr and F. W. Luscinskas. 1993. Intravenous interleukin-8 inhibits granulocyte emigration from rabbit mesenteric venules without altering L-selectin expression or leukocyte rolling. J. Immunol. 151:6347-6357.

Lima, F. S., R. S. Bisinotto, E. S. Ribeiro, L. F. Greco, H. Ayres, M. G. Favoreto, M. R. Carvalho, K. N. Galvao and J. E. Santos. 2013. Effects of 1 or 2 treatments with prostaglandin F(2)alpha on subclinical endometritis and fertility in lactating dairy cows inseminated by timed artificial insemination. J. Dairy Sci. 96:6480-6488.

Mitchell, G. B., B. N. Albright and J. L. Caswell. 2003. Effect of interleukin-8 and granulocyte colony-stimulating factor on priming and activation of bovine neutrophils. Infect. Immun. 71:1643-1649.

NRC. 2001. Nutrient Requirements of Dairy Cattle. (7th rev. ed.) Natl. Academy Press, Washington, D.C.

Paape, M., J. Mehrzad, X. Zhao, J. Detilleux and C. Burvenich. 2002. Defense of the bovine mammary gland by polymorphonuclear neutrophil leukocytes. J. Mammary Gland Biol. Neoplasia. 7:109-121.

Watanabe, A., J. Hirota, S. Shimizu, S. Inumaru and K. Kimura. 2012. Single intramammary infusion of recombinant bovine interleukin-8 at dry-off induces the prolonged secretion of leukocyte elastase, inflammatory lactoferrin-derived peptides, and interleukin-8 in dairy cows. Vet. Med. Int. 2012:172072.

What is claimed is:

1. A method for inhibiting the development of puerperal metritis in a non-human female mammal comprising administering to the female mammal an effective amount of Interleukin-8 (IL-8), wherein the female mammal is within twenty weeks post parturition when the IL-8 is administered.

2. The method of claim 1, wherein the administration of the IL-8 is an intrauterine administration or an intravaginal administration.

3. The method of claim 1, wherein the female mammal is a member of a population of female mammals of the same species, the method further comprising administering the IL-8 to other members of the population within twenty weeks post parturition, such that inhibition of the development of puerperal metritis occurs in the other members subsequent to the administration.

4. The method of claim 1, wherein the mammal is a bovine mammal.

5. The method of claim 4, wherein the bovine mammal is a dairy cow.

* * * * *

SEQUENCE LISTING

<160> NUMBER OF SEQ ID NOS: 11

<210> SEQ ID NO 1
<211> LENGTH: 101
<212> TYPE: PRT
<213> ORGANISM: Bos taurus

<400> SEQUENCE: 1

Met Thr Ser Lys Leu Ala Val Ala Leu Leu Ala Ala Phe Leu Leu Ser
1               5                   10                  15

Ala Ala Leu Cys Glu Ala Ala Val Leu Ser Arg Met Ser Thr Glu Leu
            20                  25                  30

Arg Cys Gln Cys Ile Lys Thr His Ser Thr Pro Phe His Pro Lys Phe
        35                  40                  45

-continued

```
Ile Lys Glu Leu Arg Val Ile Glu Ser Gly Pro His Cys Glu Asn Ser
    50                  55                  60

Glu Ile Ile Val Lys Leu Thr Asn Gly Asn Glu Val Cys Leu Asn Pro
 65                  70                  75                  80

Lys Glu Lys Trp Val Gln Lys Val Val Gln Val Phe Val Lys Arg Ala
                 85                  90                  95

Glu Lys Gln Asp Pro
            100

<210> SEQ ID NO 2
<211> LENGTH: 32
<212> TYPE: DNA
<213> ORGANISM: artificial sequence
<220> FEATURE:
<223> OTHER INFORMATION: primer

<400> SEQUENCE: 2
cggcgccgtg ctgtctcgta tgtccaccga ac                              32

<210> SEQ ID NO 3
<211> LENGTH: 31
<212> TYPE: DNA
<213> ORGANISM: artificial sequence
<220> FEATURE:
<223> OTHER INFORMATION: primer

<400> SEQUENCE: 3
gctcgagtca cggatcttgt ttttctgcac g                               31

<210> SEQ ID NO 4
<211> LENGTH: 101
<212> TYPE: PRT
<213> ORGANISM: Bubalus bubalus

<400> SEQUENCE: 4

Met Thr Ser Lys Leu Ala Val Ala Leu Leu Ala Ala Phe Leu Leu Ser
 1               5                  10                  15

Ala Ala Leu Cys Glu Ala Ala Val Leu Ser Arg Met Ser Thr Glu Leu
                 20                  25                  30

Arg Cys Gln Cys Ile Lys Thr His Ser Thr Pro Phe His Pro Lys Phe
             35                  40                  45

Ile Lys Glu Leu Arg Val Ile Glu Ser Gly Pro His Cys Glu Asn Ser
    50                  55                  60

Glu Ile Ile Val Lys Leu Thr Asn Gly Lys Glu Val Cys Leu Asn Pro
 65                  70                  75                  80

Lys Glu Lys Trp Val Gln Lys Val Val Gln Val Phe Val Lys Arg Ala
                 85                  90                  95

Glu Lys Gln Asp Pro
            100

<210> SEQ ID NO 5
<211> LENGTH: 101
<212> TYPE: PRT
<213> ORGANISM: CERVUS ELEPHUS

<400> SEQUENCE: 5

Met Thr Ser Lys Leu Ala Val Ala Leu Leu Ala Ala Phe Leu Leu Ser
 1               5                  10                  15

Ala Ala Leu Cys Glu Ala Ala Val Leu Ser Arg Met Ser Thr Glu Leu
                 20                  25                  30
```

-continued

Arg Cys Gln Cys Ile Lys Thr His Ser Thr Pro Phe His Pro Lys Phe
            35                  40                  45

Ile Lys Glu Leu Arg Val Ile Glu Ser Gly Pro His Cys Glu Asn Ser
 50                  55                  60

Glu Ile Ile Val Lys Leu Thr Asn Gly Lys Glu Val Cys Leu Asn Pro
 65                  70                  75                  80

Lys Glu Lys Trp Val Gln Lys Val Val Glu Val Phe Val Lys Arg Ala
                85                  90                  95

Glu Lys Gln Asp Pro
            100

<210> SEQ ID NO 6
<211> LENGTH: 101
<212> TYPE: PRT
<213> ORGANISM: Ovis aries

<400> SEQUENCE: 6

Met Thr Ser Lys Leu Ala Val Ala Leu Leu Ala Phe Leu Leu Ser
 1                5                  10                  15

Ala Ala Leu Cys Glu Ala Ala Val Leu Ser Arg Met Ser Thr Glu Leu
                20                  25                  30

Arg Cys Gln Cys Ile Lys Thr His Ser Thr Pro Phe His Pro Lys Phe
            35                  40                  45

Ile Lys Glu Leu Arg Val Ile Glu Ser Gly Pro His Cys Glu Asn Ser
 50                  55                  60

Glu Ile Ile Val Lys Leu Thr Asn Gly Lys Glu Val Cys Leu Asp Pro
 65                  70                  75                  80

Lys Glu Lys Trp Val Gln Lys Val Val Gln Ala Phe Leu Lys Arg Ala
                85                  90                  95

Glu Lys Gln Asp Pro
            100

<210> SEQ ID NO 7
<211> LENGTH: 97
<212> TYPE: PRT
<213> ORGANISM: Equus caballus

<400> SEQUENCE: 7

Met Thr Ser Lys Leu Ala Val Ala Leu Leu Ala Val Phe Leu Leu Ser
 1                5                  10                  15

Ala Ala Leu Cys Glu Ala Ala Val Val Ser Arg Ile Thr Ala Glu Leu
                20                  25                  30

Arg Cys Gln Cys Ile Lys Thr His Ser Lys Pro Phe Asn Pro Lys Leu
            35                  40                  45

Ile Lys Glu Met Arg Val Ile Glu Ser Gly Pro His Cys Glu Asn Ser
 50                  55                  60

Glu Ile Ile Val Lys Leu Val Asn Gly Ala Glu Val Cys Leu Asn Pro
 65                  70                  75                  80

His Thr Lys Trp Val Gln Ile Ile Val Gln Ala Phe Leu Lys Arg Thr
                85                  90                  95

Glu

<210> SEQ ID NO 8
<211> LENGTH: 100
<212> TYPE: PRT
<213> ORGANISM: Homo sapiens

<400> SEQUENCE: 8

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser Leu
            100

<210> SEQ ID NO 9
<211> LENGTH: 101
<212> TYPE: PRT
<213> ORGANISM: Canis lupus familiaris

<400> SEQUENCE: 9

Met Thr Ser Lys Leu Ala Val Ala Leu Leu Ala Ala Phe Val Leu Ser
1               5                   10                  15

Ala Ala Leu Cys Glu Ala Ala Val Leu Ser Arg Val Ser Ser Glu Leu
                20                  25                  30

Arg Cys Gln Cys Ile Lys Thr His Ser Thr Pro Phe His Pro Lys Tyr
            35                  40                  45

Ile Lys Glu Leu Arg Val Ile Asp Ser Gly Pro His Cys Glu Asn Ser
    50                  55                  60

Glu Ile Ile Val Lys Leu Phe Asn Gly Asn Glu Val Cys Leu Asp Pro
65                  70                  75                  80

Lys Glu Lys Trp Val Gln Lys Val Val Gln Ile Phe Leu Lys Lys Ala
                85                  90                  95

Glu Lys Gln Asp Pro
            100

<210> SEQ ID NO 10
<211> LENGTH: 101
<212> TYPE: PRT
<213> ORGANISM: Felus catus

<400> SEQUENCE: 10

Met Thr Ser Lys Leu Val Val Ala Leu Leu Ala Ala Phe Met Leu Ser
1               5                   10                  15

Ala Ala Leu Cys Glu Ala Ala Val Leu Ser Arg Ile Ser Ser Glu Leu
                20                  25                  30

Arg Cys Gln Cys Ile Lys Thr His Ser Thr Pro Phe Asn Pro Lys Leu
            35                  40                  45

Ile Lys Glu Leu Thr Val Ile Asp Ser Gly Pro His Cys Glu Asn Ser
    50                  55                  60

Glu Ile Ile Val Lys Leu Val Asn Gly Lys Glu Val Cys Leu Asp Pro
65                  70                  75                  80

Lys Gln Lys Trp Val Gln Lys Val Val Glu Ile Phe Leu Lys Lys Ala
                85                  90                  95

Glu Lys Gln Asn Ala
            100
```

```
<210> SEQ ID NO 11
<211> LENGTH: 101
<212> TYPE: PRT
<213> ORGANISM: artificial sequence
<220> FEATURE:
<223> OTHER INFORMATION: consensus IL-8 based on sequences in Figure 15
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 11

Met Thr Ser Lys Leu Ala Val Ala Leu Leu Ala Ala Phe Leu Leu Ser
1               5                   10                  15

Ala Ala Leu Cys Glu Ala Ala Val Leu Ser Arg Xaa Ser Xaa Glu Leu
            20                  25                  30

Arg Cys Gln Cys Ile Lys Thr His Ser Thr Pro Phe His Pro Lys Phe
        35                  40                  45

Ile Lys Glu Leu Arg Val Ile Glu Ser Gly Pro His Cys Glu Asn Ser
    50                  55                  60

Glu Ile Ile Val Lys Leu Xaa Asn Gly Lys Xaa Val Cys Leu Xaa Pro
65                  70                  75                  80

Lys Glu Lys Trp Val Gln Lys Val Val Gln Val Phe Leu Lys Arg Ala
                85                  90                  95

Glu Lys Gln Asp Pro
            100
```